United States Patent
Bietz et al.

(10) Patent No.: US 10,319,247 B2
(45) Date of Patent: Jun. 11, 2019

(54) AERIAL VEHICLE NAVIGATION METHOD

(71) Applicants: Steven Lee Bietz, Cypress, TX (US); Clinton Courier, Cotati, CA (US)

(72) Inventors: Steven Lee Bietz, Cypress, TX (US); Clinton Courier, Cotati, CA (US)

(73) Assignee: Voll, Inc., Cypress, TX (US)

( * ) Notice: Subject to any disclaimer, the term of this patent is extended or adjusted under 35 U.S.C. 154(b) by 87 days.

(21) Appl. No.: 15/482,872

(22) Filed: Apr. 10, 2017

(65) Prior Publication Data

US 2017/0287343 A1 Oct. 5, 2017

Related U.S. Application Data

(63) Continuation-in-part of application No. 15/086,204, filed on Mar. 31, 2016, now Pat. No. 10,149,634, and
(Continued)

(51) Int. Cl.
| | | |
|---|---|---|
| *G08G 5/00* | (2006.01) | |
| *A61B 8/08* | (2006.01) | |
| *B64C 39/02* | (2006.01) | |
| *B64D 47/08* | (2006.01) | |
| *G06K 9/00* | (2006.01) | |
| *H04B 1/3877* | (2015.01) | |
| *H04B 1/3888* | (2015.01) | |
| *H04W 4/02* | (2018.01) | |
| *H04W 84/18* | (2009.01) | |
| *H04W 4/80* | (2018.01) | |
| *B60L 53/14* | (2019.01) | |
| *B60L 53/80* | (2019.01) | |

(Continued)

(52) U.S. Cl.
CPC ............. *G08G 5/0069* (2013.01); *A61B 8/08* (2013.01); *B60L 53/14* (2019.02); *B60L 53/80* (2019.02); *B64C 39/024* (2013.01); *B64D 47/08* (2013.01); *G06K 9/0063* (2013.01); *H04B 1/3877* (2013.01); *H04B 1/3888* (2013.01); *H04W 4/023* (2013.01); *H04W 4/80* (2018.02); *H04W 84/18* (2013.01); *B64C 2201/042* (2013.01); *B64C 2201/127* (2013.01); *G01C 21/206* (2013.01); *G08C 17/02* (2013.01)

(58) Field of Classification Search
CPC ...... G08G 5/0069; A61B 8/08; B60L 11/1816
See application file for complete search history.

(56) References Cited

U.S. PATENT DOCUMENTS

| | | |
|---|---|---|
| 2011/0195753 A1 | 8/2011 | Mock et al. |
| 2013/0033358 A1 | 2/2013 | Yamazaki et al. |
| | (Continued) | |

OTHER PUBLICATIONS

Vincent Chan and Anahi Perlas, Basics of Ultrasound Imaging, S.N. Narouze (ed.), Atlas of Ultrasound-Guided Procedures in Interventional Pain Management, DOI 10.1007/978-1-4419-1681-5_2, © Springer Science+Business Media, LLC 2011, 2011, XXVIII, 372 p. 465 illus., 350 illus. in color., Hardcover, ISBN: 978-1-4419-1679-2.

*Primary Examiner* — Basil T. Jos
(74) *Attorney, Agent, or Firm* — Tracy Jong Law Firm; Tracy P. Jong; Cheng Ning Jong

(57) ABSTRACT

A method for navigating an aerial vehicle from a first location to a second location, wherein the aerial vehicle having a localization system, the method including guiding the aerial vehicle according to a ground navigation map from the first location to the second location.

17 Claims, 28 Drawing Sheets

Related U.S. Application Data a continuation-in-part of application No. 15/357,660, filed on Nov. 21, 2016, now Pat. No. 9,651,651.

(51) Int. Cl.
    *G08C 17/02*     (2006.01)
    *G01C 21/20*     (2006.01)

(56) References Cited

U.S. PATENT DOCUMENTS

2013/0146661 A1    6/2013   Melbrod et al.
2016/0207637 A1*   7/2016   Campillo .............. B64C 39/024

\* cited by examiner

AERIAL VEHICLE NAVIGATION METHOD

PRIORITY CLAIM AND RELATED APPLICATIONS

This continuation-in-part application claims the benefit of priority from application U.S. Ser. No. 15/086,204 filed on Mar. 31, 2016 and U.S. Ser. No. 15/357,660 filed on Nov. 21, 2016. Each of said applications is incorporated by reference in its entirety.

BACKGROUND OF THE INVENTION

1. The Field of the Invention

The present invention is directed generally to navigation methods of aerial vehicles. More specifically, the present invention is directed to navigation methods of aerial vehicles that are tied to ground navigation data and/or ground traffic infrastructure.

2. Background Art

Modern day localization methods typically involve the use of Global Positioning System (GPS) which require hardware, e.g., GPS receiver, cell towers, relay towers and other infrastructure to locate immobile or mobile devices. Such methods are not available to underwater applications and can be non-operational on severely overcast days.

U.S. Pat. Pub. No. 20130033358 of Yamazaki et al. (hereinafter Yamazaki) discloses a system including at least one sender, and a beacon signal sent from the sender that is received by a portable terminal. In accordance with a sender ID included in the beacon signal, the portable terminal displays on an Liquid Crystal Display (LCD) a map image and a current position of the portable terminal or a user having the portable terminal, and displays on the LCD a guide image as for events or exhibition items in a predetermined place. The portable terminal stores state information included in the beacon signal for each sender (sender ID), and transmits or moves the state information to a central terminal at a predetermined timing. Yamazaki fails to disclose a case capable of physical coupling to a mobile device. Yamazaki further fails to disclose a means by which to detect a large motion or movement and guard against detecting vibrations which are to be ignored. This publication fails to include a mesh network in that senders/nodes do not relay information between each other but only to a portable terminal. Further, the portable terminals do not relay information between each other and are not able to relay information from one terminal to another and back to the central terminal. A mobile terminal is unable to communicate directly to the central terminal. Thus, if a portable terminal loses communication, it cannot relay through another portable terminal. Note also in this disclosure that vibration is used to detect that a sender or node has been moved from a stationary position. A notice of vibration or movement indicates that repositioning and recalibration of Yamazaki's portable terminal is required while the present invention includes senders or nodes that can be continuously moving (as not required to be stationary). Yamazaki fails to disclose localization methods.

U.S. Pat. Pub. No. 20130146661 of Melbrod et al. (hereinafter Melbrod) discloses embodiments of a smart phone casing and information exchange system which enables a user to carry a single system that merges the digital and telecommunications necessities of the individual with the personalized cards, membership accounts, consumer credit and/or medical insurance or health information in a single source protected both physically with a hardened case, and digitally with appropriate safeguards for electronic protection. Melbrod demonstrates the use of a smart phone case capable of storing information and safeguards for allowing certain information exchanges only. It does not however disclose a smart phone case having the tools and means for detecting large motions and movements, etc. Melbrod also fails to disclose localization methods.

U.S. Pat. Pub. No. 20110195753 of Mock et al. (hereinafter Mock) discloses a smart phone case with Light Emitting Diodes (LEDS). In a particular embodiment, the case includes a front portion adapted to cradle a lower portion of a smart phone, a rear portion adapted to engagingly mate with the front portion to secure the smart phone within the case, a first strip of LEDS and a second strip of LEDS that are mounted on opposing sides of the front portion, a vibrating sensor that is adapted to activate the LEDS of the case when a vibrator of the smart phone is vibrating, and circuitry is used to control the vibrating sensor and the LEDS. The vibrating sensor detects vibrations of the vibrator of the smart phone when the smart phone is receiving an incoming call or message. The LEDS are programmed to display in a set sequence when activated, where the set sequence to display the LEDS is selected by a user. Mock demonstrates the use of a case for detecting vibration from a smart phone and taking an action, i.e., activating LEDS based on the detection of the vibration. It does not however disclose a smart phone case having the tools and means for detecting large motion and movements, etc. Mock also fails to disclose localization methods.

There have been numerous restrictions imposed by the Federal Aviation Administration (FAA) upon an operator of a drone or an unmanned aerial vehicle both for personal and commercial purposes. Chief concerns have been the privacy and safety of those that live and work within the environment the aerial vehicle operates. Among other commercial operating rules, an operator must keep the aircraft or aerial vehicle in sight, i.e., a visual line-of-sight must be maintained between the operator and the aerial vehicle. However, manually-controlled flights may become commercially impractical in the future as a ground pilot may only be able to control one aerial vehicle at a time and the skill level required of the pilot may be economically unattainable.

Therefore, there arises a need for a localization method which can be seamlessly utilized with a ubiquitous mobile device for providing a localization system at low costs and one that is not dependent on a Global Positioning System (GPS) network. There also arises a need for automated navigation or flights of aerial vehicle, especially those involved with delivery of light-weight goods.

SUMMARY OF THE INVENTION

Disclosed herein is a method for navigating an aerial vehicle from a first location to a second location, wherein the aerial vehicle includes a localization system. The method includes guiding the aerial vehicle according to a ground navigation map from the first location to the second location.

In one embodiment, the method further includes guiding the aerial vehicle according to markers disposed on traffic signs and ground transportation pathways.

In one embodiment, the traffic signs includes a marker fabricated from a material visible to the naked eye or a material invisible to the naked eye.

In one embodiment, the aerial vehicle includes an image processing system and a frequency receiver device. The method further includes:
(a) visually detecting a feature indicating an opening upon arriving at an intermediate location between the first location and the second location;
(b) visually guiding the aerial vehicle through the opening from the intermediate location;
(c) upon passing the opening, functionally engaging a frequency receiver device of the aerial vehicle with at least three frequency originator devices of known location to yield a relative location of the aerial vehicle with respect to the at least three frequency originator devices; and
(d) guiding the aerial vehicle from the intermediate location to the second location based on closing a gap between the relative location of the aerial vehicle with respect to the at least three frequency originator devices and the second location.

In one embodiment, the aerial vehicle includes an image processing system and a frequency receiver device. The method further includes:
(a) visually detecting a feature indicating an opening upon arriving at an intermediate location between the first location and the second location;
(b) visually guiding the aerial vehicle through the opening from the intermediate location; and
(c) upon passing the opening, detecting an image of a pattern and upon detecting the pattern, guiding the aerial vehicle to close a gap between the aerial vehicle and the pattern.

In one embodiment, the aerial vehicle further includes a short range wireless communication tool. The method further includes guiding the aerial vehicle towards the source of a short range wireless communication signal at the second location.

In one embodiment, the method further includes guiding the aerial vehicle to a location between the first location and the second location for power replenishment such that the aerial vehicle completes its journey from the first location to the second location.

It is a primary object of the present invention to provide aerial vehicle navigation methods based on ubiquitous well-proven ground navigation data and infrastructure and therefore such methods should encounter little to no privacy concerns in their implementations in various local communities.

It is another object of the present invention to provide aerial vehicle navigation methods not tied to a Global Positioning System (GPS), making such navigation methods immune to loss or unavailability of GPS data (e.g., in buildings or other interior spaces, etc.) or excessive consumption of on-board aerial vehicle power.

It is yet another object of the present invention to provide aerial vehicle navigation methods capable of guiding an aerial vehicle to an interior space, therefore enabling the aerial vehicle to perform delivery tasks directly to recipients of delivery services.

Whereas there may be many embodiments of the present invention, each embodiment may meet one or more of the foregoing recited objects in any combination. It is not intended that each embodiment will necessarily meet each objective. Thus, having broadly outlined the more important features of the present invention in order that the detailed description thereof may be better understood, and that the present contribution to the art may be better appreciated, there are, of course, additional features of the present invention that will be described herein and will form a part of the subject matter of this specification.

BRIEF DESCRIPTION OF THE DRAWINGS

The accompanying drawings, which are incorporated in and constitute a part of this specification, illustrate embodiments and together with the description, serve to explain the principles of the methods and systems.

PARTS LIST

Figure 1:
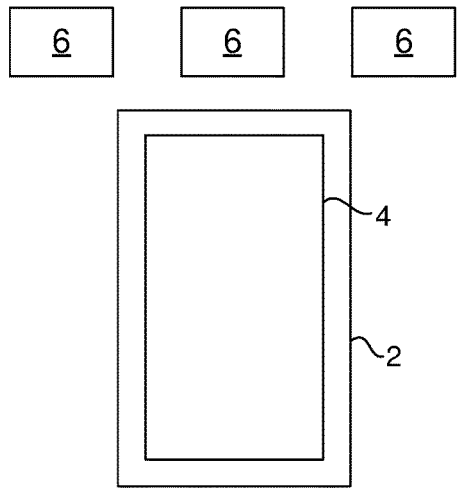
FIG. 1 is a block diagram depicting a communication system where a mobile device case is attached to a mobile device and a plurality of sensors is disposed remotely from the mobile device case.

2—mobile device case
4—mobile device
6—sensor
8—communication between mobile device case and sensor
10—communication between mobile device case and mobile device
12—communication between mobile device cases
14—communication between mobile devices
16—communication between mobile device and sensor
18—radius of trajectory of sensor C
20—distance between sensor A and mobile device case B
22—distance between mobile device case B and sensor C
24—total distance between sensor A and sensor C
26—communication between sensors
28—step of synchronizing clock time
30—step of sending message with time stamp of transmit time
32—step of sending message with time stamp of transmit time and calculated time of flight
34—step of calculating time of flight
36—plane
38—subgroup
40—quality check
42—first frequency originator device
44—second frequency originator device
46—broadcast signal having first frequency
48—broadcast signal having second frequency
50—frequency originator device, e.g., long range acoustic device (LRAD)
52—arc representing distance from frequency originator device
54—frequency receiver device, e.g., mobile device
56—first frequency receiver device
58—second frequency receiver device
60—distance between first frequency originator device and first frequency receiver device
62—distance between first frequency originator device and second frequency receiver device
64—distance between second frequency originator device and first frequency receiver device
66—distance between second frequency originator device and second frequency receiver device
68—distance between first and second frequency receiver devices on a mobile device
70—correction
72—axis connecting first and second frequency originator devices
74—information storage device
76—vehicle
78—visually unique object
80—frequency originator device
82—image acquisition device
84—visually unique pattern
86—relative location or derived distance and orientation of frequency receiver device relative to visually unique pattern
88—image of delivery portal
90—marker
92—support structure, e.g., tower, building
94—frequency receiver device
96—building
98—background features
100—traffic control device
102—delivery
104—delivery portal
106—passageway
108—window
110—delivery dispense control device
112—roadway
114—charging station 116—charger
118—infrared paint indicating location of charging station
120—infrared paint indicating roadway directions
122—infrared paint indicating distance to the next traffic sign
124—infrared paint indicating structure is a charging station
126—deliverable or load

PARTICULAR ADVANTAGES OF THE INVENTION

The present aerial vehicle navigation methods are based on ubiquitous, well-proven ground navigation data and traffic infrastructure and therefore they should encounter little to no privacy concerns in their implementations in various local communities.

In one embodiment, the present aerial vehicle navigation methods are not tied to a Global Positioning System (GPS), making such navigation methods immune to loss or unavailability of GPS data (e.g., inside buildings or other interior spaces, etc.) or excessive consumption of on-board aerial vehicle power.

Currently disclosed aerial vehicle navigation methods are capable of guiding an aerial vehicle to an interior space, therefore enabling the aerial vehicle to perform delivery tasks directly to recipients of delivery services.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive, as claimed.

DETAILED DESCRIPTION OF A PREFERRED EMBODIMENT

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower). The terms "large motion" or "large movement" are used herein to mean a movement that is sufficient large, e.g., as a result of the opening or closing of a door, a position shift of about 5% per second, a position shift of at least about 1 inch per second, etc. A vibration caused by the operation of a common household appliance or air movement due to forced circulations in an indoor space shall not be considered to have the capability of causing a large motion or large movement (excluding some devices such as washing machines and clothes driers).

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. "Optional" or "optionally" means that the subsequently described event or circumstance may or may not occur, and that the description includes instances where said event or circumstance occurs and instances where it does not. Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the examples included therein and to the figures and their previous and following description.

FIG. 1 is a block diagram depicting a communication system where a mobile device case is attached to a mobile device 4 and a plurality of sensors 6 is disposed remotely from the mobile device case 2. The mobile device case 2 is physically and functionally coupled to the mobile device 4. In one embodiment, the mobile device case 2 is a cradle in which the mobile device is seated such that the mobile device case 2 provides protection against accidental impact, etc. A mobile device case 2 is essentially a controller capable of communication with a mobile device 4 and one or more sensors 6. "Communication," as used herein is defined as communication via various communication means and protocols, e.g., Bluetooth, Global Positioning System (GPS), wireless local area network (Wi-Fi), etc. In one embodiment, an application capable of being installed in a mobile device is provided to cause the mobile device, via its transmitter and receiver, to communicate with a mobile device case 2 and a sensor 6. Each mobile device case 2 and sensor 6 may alternatively be equipped with a controller, transmitter and receiver to facilitate communication of one of these devices with another device. In one embodiment, a sensor 6 is an accelerometer between 2 g-8 g. In another embodiment, a sensor 6 is a 3-axis digital gyro with programmable full-scale ranges of about ±250, ±500, ±1000, and ±2000 degrees/sec (dps), which is useful for precision tracking of both fast and slow motions. In yet another embodiment, a sensor 6 is a low-power digital three dimensional (3D) magnetic sensor capable of measuring local magnetic fields up to about 10 Gauss with output data rates (ODR) up to 80 Hz. In one embodiment, a receiver is a device capable of receiving signals or messages transmitted as waves (e.g., radio and sound, etc.) having a frequency response falling within or outside that of the frequency response of a typical microphone which ranges from about 20 Hz to about 20 kHz.

Figure 2:
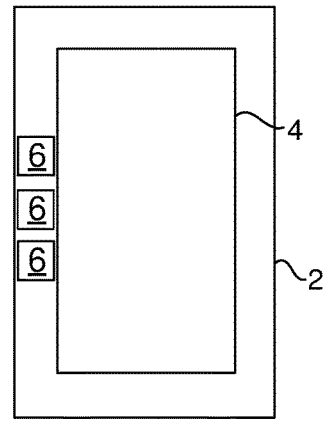
FIG. 2 is a block diagram depicting a communication system where a mobile device case is attached to a mobile device and a plurality of sensors are coupled to the mobile device case.

FIG. 2 is a block diagram depicting a communication system where a mobile device case 2 is attached to a mobile device and a plurality of sensors 6 are coupled to the mobile device case 2. In one embodiment, a mobile device case 2 comprises a plurality of sensors 6. In another embodiment, a plurality of sockets are made available on-board the mobile device case 2 and configured for receiving sensors 6. In use, only the necessary sensors 6 are inserted in the sockets and functionally connected to the mobile device case 2.

Figure 3:
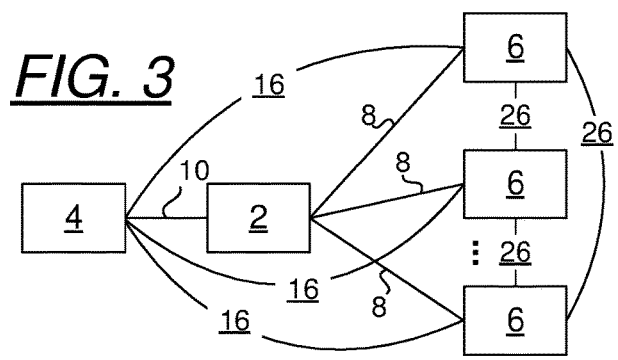
FIG. 3 is a block diagram depicting a mobile device, a mobile device case, a plurality of sensors and the relationships between these components.

FIG. 3 is a block diagram depicting a mobile device 4, a mobile device case 2, a plurality of sensors 6 and the relationships between these components. The mobile device 4 is configured to communicate with the mobile device case 2 via communication 10 and each of the sensors 6 via communication 16. The mobile device case 2 is configured to communicate with each of the sensors 6 via communication 8. A mobile device case 2 may communicate with another mobile device case 2 via communication 12. A mobile device 4 may communicate with another mobile device 4 via communication 14. A sensor 26 may be configured to communicate with another sensor via communication 26. In one embodiment, the present system includes an application adapted to a mobile device 4 and at least one sensor 6. In another embodiment, the present system includes an application adapted to a mobile device 4, at least one mobile device case 2 and at least one sensor 6.

Figure 4:
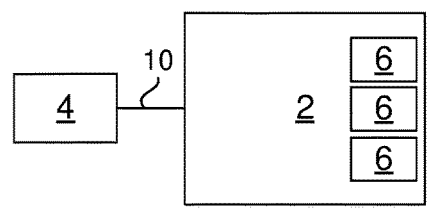
FIG. 4 is a block diagram depicting a mobile device, a mobile device case, a plurality of sensors coupled to the mobile device case and the relationships between these components.

FIG. 4 is a block diagram depicting a mobile device 4, a mobile device case 2, a plurality of sensors 6 coupled to the mobile device case 2 and the relationships between these components. In one embodiment, the sensors communicates directly with the mobile device case 2 as if the sensors 6 are directly wired to the mobile device case 2 when the sensors are seated in the sockets of mobile device case 2. In another embodiment, the sensors 6 communicate wirelessly to the mobile device case 2 as if the sensors are mounted wirelessly from the mobile device case 2.

Figure 5:
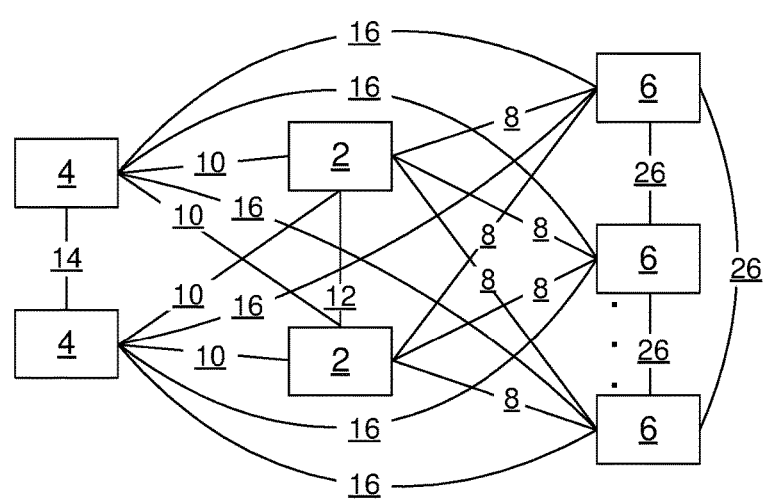
FIG. 5 is a block diagram depicting two sets of mobile device and mobile device case, a plurality of sensors and the relationships between these components.

FIG. 5 is a block diagram depicting two sets of mobile device 4 and mobile device case 2, a plurality of sensors 6 and the relationships between these components. This diagram is provided essentially to demonstrate that, in addition to communicating between dissimilar devices, communication may also occur between components of the same make, i.e., a mobile device 4 to another mobile device 4 and a mobile device case 2 to another mobile device case.

Figure 6:
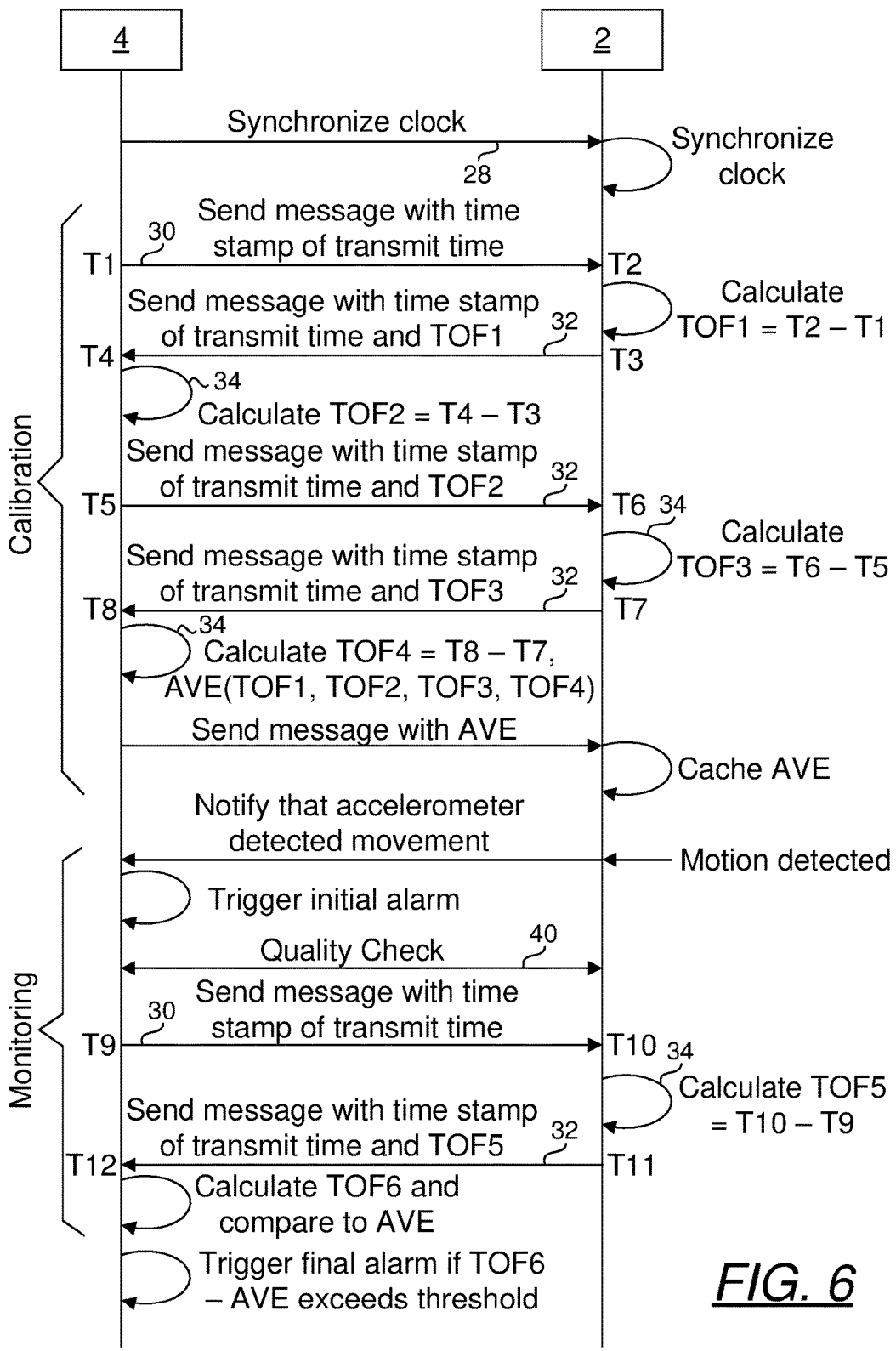
FIG. 6 is a sequence diagram depicting a means by which a mobile device case is used in conjunction with a mobile device to detect a movement of the mobile device case.

FIG. 6 is a sequence diagram depicting a means by which a mobile device case 2 is used in conjunction with a mobile device to detect a movement of the mobile device case 2. The system for carrying out such detection includes a mobile device case 2, a mobile device 4 and an accelerometer capable of detecting motion of the mobile device case 2. In this example, the mobile device case 2 is used to detect and verify a movement of the mobile device case 2 that is considered sufficiently severe to warrant an action to alert a user. The mobile device case 2 is attached to an object, the motion of which is to be detected while the mobile device 4 is placed in the vicinity the user such that the user can be alerted via an output of the mobile device 4. The mobile device 4 first initiates clock synchronization (step 28) with the mobile device case 2 by sending its clock time to the mobile device case 2. The time stamp at which the clock time starts to be transmitted is assumed to be the clock time. As it takes a finite amount of time for such transmission to be received at the mobile device case, the time at which such transmission to be received at the mobile device case 2 is no longer the clock time. The mobile device case thus sets its clock time with a time that corresponds to the clock time received and the duration for the clock time to be transmitted. Alternatively, the mobile device case 2 may initiate clock time synchronization. Upon synchronizing the clock of the mobile device case 2, the mobile device case 2 and the mobile device 4 are ready for a calibration process which involves averaging the time of flight of a message between the two devices 2, 4. The mobile device 4 initiates calibration by sending a message with the time stamp at which the message is started to be transmitted as in step 30. Upon receipt of the message, the mobile device case 2 then calculates (step 34) the time of flight of the message, i.e., the time it takes for the message to be transmitted from the mobile device 4 to the mobile device case 2 (time of flight). This is followed by a transmission from the mobile device case 2 which includes the time stamp at which a message started to be transmitted and the time of flight just calculated as shown in step 32. Upon receipt of the message, the mobile device 4 then calculates the time of flight of the message. The process of enabling the calculation of a time of flight by one device (by making available the time stamp of a transmission) in another device, the process of calculating the time of flight of a message by another device and the process of notifying another device of the time of flight is repeated until a satisfactory number of transmissions between the devices or until a satisfactory average of time of flight has been obtained. A satisfactory average of time of flight may be one which is tied to a satisfactory standard deviation. In this example, the calibration concludes with the averaging of four values of time of flight. The time of flight data is made available in both of the devices 2, 4. Alternatively, the time of flight and the average time of flight data may be retained in one of the two devices and the average time of flight data is only made available to the device which requires it. After the time of flight has been calculated, the mobile device case 2 is now ready to detect motion.

In order to eliminate false detection, the system must detect a motion warranting a response from the user in conjunction with the time of flight data indicating a distance change has occurred. A triggering of the accelerometer signals that a motion has been detected and a notification is sent from the mobile device case 2 to the mobile device 4. This event marks the start of the monitoring phase of the sequence. An initial alarm may be emitted to the user signaling the detection a motion has been detected in the mobile device case 2. Alternatively, the monitoring phase may start immediately after clock synchronization has completed. Upon detecting a motion with the accelerometer, a question remains as to whether or not the motion is caused by an action which warrants a response at either the mobile device 4 or the mobile device case 2. Upon receiving the notification from the mobile device case 2, the mobile device 4 initiates a process where one or more values of the time of flight are obtained. The process in getting a time of flight value is similar to the process in which a time of flight value is calculated in the calibration process. As the time of flight of a message corresponds the distance between the mobile device case 2 and the mobile device 4, a movement in the mobile device case 2 causes the time of flight of a message transmitted between the two changes. Therefore, a significant deviation of the time of flight from the average time of flight previously established in the calibration process may signal a large change in the position of the mobile device case 2 and an alarm may be triggered at the mobile device 4 to indicate such event. If an additional device, such as a sensor 6 or a mobile device case 2 were to be added to the network, clock synchronization may be performed to the entire network or to the newly added device alone. A request for clock synchronization may be initiated via the device to be added. In one embodiment, such request is actuated via a button functionally connected to such request. Although the example depicted in FIG. 6 includes a mesh network of a mobile device case 2 and a mobile device 4, two or more mobile devices 4 may be used in place of the combination of a mobile device case 2 and a mobile device 4. In general, the type of clock time synchronization is selected based on the proximity of the devices involved to each other. In an embodiment where devices are disposed in close proximity, mobile devices are synchronized via a peer-to-peer mechanism. A peer-to-peer mechanism includes, but not limited to, the use of a Near Field Communication (NFC), Bluetooth or Wi-Fi, etc. transmit-receive pair to transmit the clock time and transmit time of a first mobile device to a second mobile device where its clock is reconciled with the clock time of the first mobile device. In an embodiment where devices are disposed apart at great distances, mobile devices clock time synchronization may be synchronized via a web server. The clock time and transmit time of a first mobile device are transmitted via a web connection to a second mobile device where its clock is reconciled with the clock time of the first mobile device. A web server may be accessed via a mobile device wirelessly or by hard wire.

In order to determine to a high degree of certainty that a large motion has indeed occurred, a quality check 40 including the following two quality checks may be performed.

An Example of a Quality Check for Confirming that a Movement has Begun

Just after the initial distance between devices is determined (first measurement after any calibration loop), the device can be disposed in a stand-by mode to conserve power. If the accelerometer detects a movement while in standby mode, the device having the accelerometer wakes up and starts to send time data such that time of flight (TOF) data can be calculated in the device receiving the time data. The accelerometer serves here to both provide a confirmation of movement and allow for a power conserving standby mode. In the event that environmental factors may give difficult signal readings (e.g., moving steel objects that could cause signal reflections that could falsely be interpreted as movement), such quality check can reduce extraneous or unreliable time data. The use of a standby mode allows for less power usage by only making transmissions when movement begins. It is important to note here that both devices in a two device system of a phone and a sensor could use sleep mode, but TOF calculations need to begin if either one of the two begins to move.

Examples of a Quality Check for when Devices are in Motion and are Regularly Making TOF Calculations Scenario A: Accelerometers in both devices compare relative speed to each other.

Scenario B: Gyros in both devices compare relative angle of movement off of horizontal between both devices.

Scenario C: Compasses in both devices compare relative directional heading between both devices.

Scenarios A, B, and C contribute to helping to maintain good relative position between devices while TOF method continues to establish relative distance, especially for use when viewed on a mobile device screen with a grid reference. Note that compass and gyro are used only to assist in orientation as in quality check and they are used for screen display/interface and do not detract from TOF.

Figure 7:
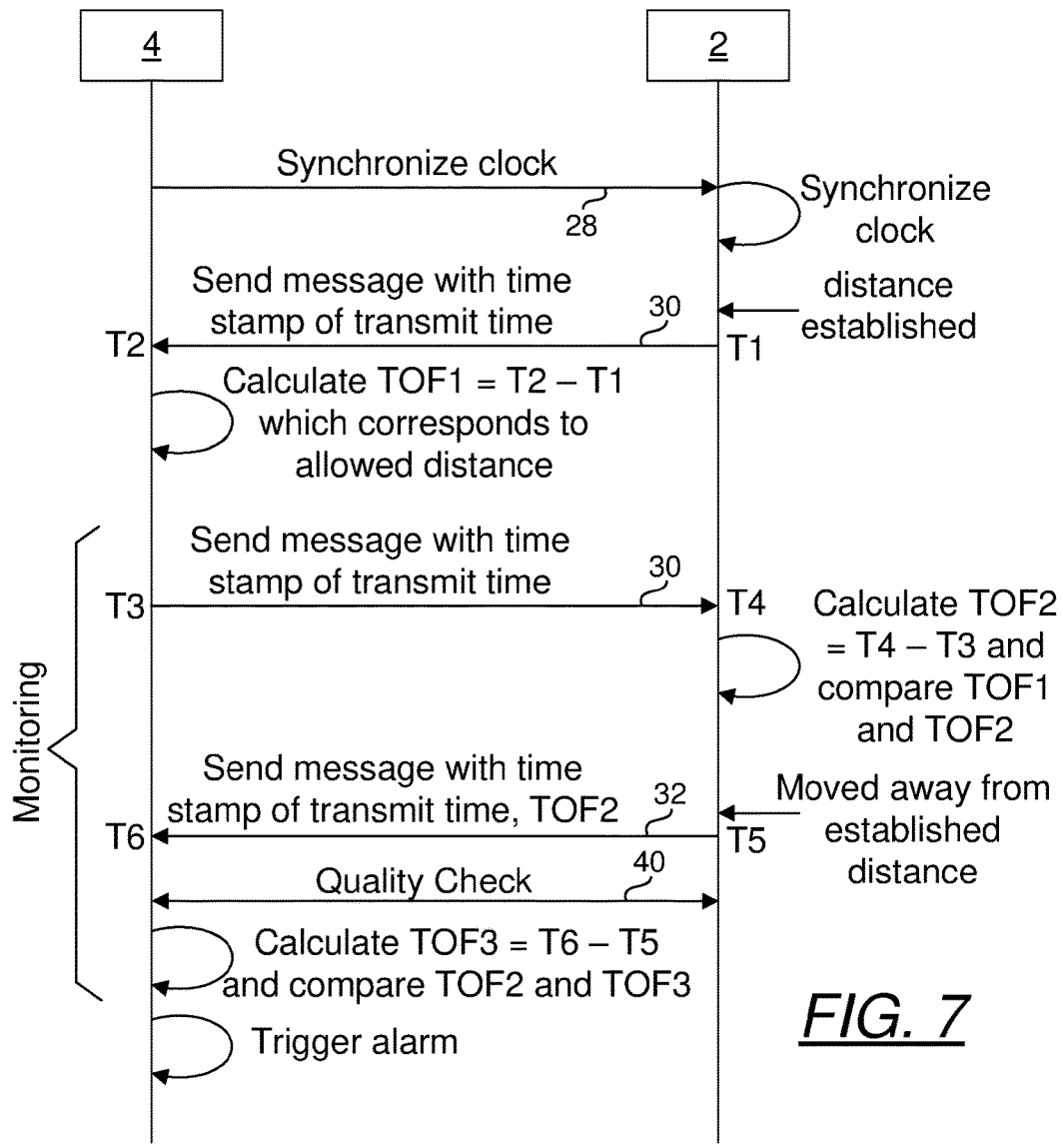
FIG. 7 is a sequence diagram depicting a means by which a mobile device case is used in conjunction with a mobile device to detect a condition where the distance between the two devices has grown beyond a predetermined threshold.

FIG. 7 is a sequence diagram depicting a means by which a mobile device case 2 is used in conjunction with a mobile device 4 to detect a case where the distance between the two devices 2, 4 has grown beyond a predetermined threshold. In one aspect, an individual to be monitored is given the mobile device case 2 while an individual monitoring the mobile device case 2 uses the mobile device 4. Again, the clocks of the two devices 2, 4 are first synchronized. Upon synchronizing the clocks in the two devices 2, 4, the devices enter a monitoring phase. Prior to the monitoring phase, a time of flight corresponding to the maximum distance allowed between the two devices must first be established. At the start of the monitoring phase, the mobile device case 2 initiates communication by sending a message with the time stamp at which the message is started to be transmitted as in step 30. Upon receipt of the message, the mobile device 4 then calculates the time of flight of the message, i.e., the time it takes to the message to be transmitted from the mobile device 4 to the mobile device case 2 (time of flight). This is followed by a transmission from the mobile device case 2 which includes the time stamp at which a message starts to be transmitted and the time of flight just calculated as shown in step 32. Upon receipt of the message, the mobile device 4 then calculates the time of flight of the message and the present time of flight is compared to the previously calculated time of flight. For simplicity, the present diagram shows only two sets of time of flight. In practice, many more sets of time of flight are obtained and analyzed. If a large discrepancy between the two values (which indicates a departure of a device from another) has been detected, an alarm may be activated to indicate such an event.

Figure 8:
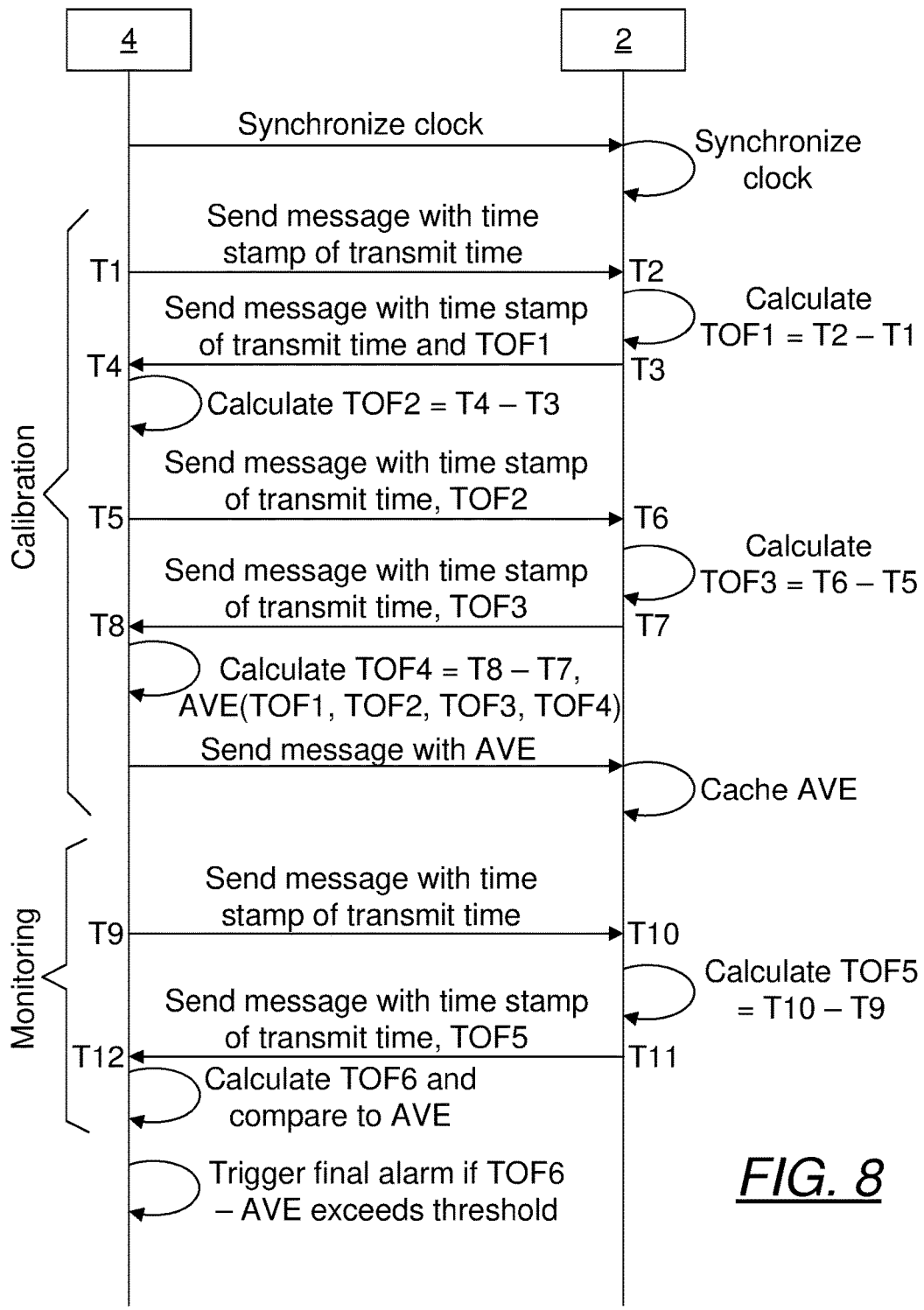
FIG. 8 is a sequence diagram depicting a means by which a mobile device case is used in conjunction with a mobile device to detect an intrusion in a space between the two devices.

FIG. 8 is a sequence diagram depicting a means by which a mobile device case 2 is used in conjunction with a mobile device 4 to detect an intrusion in a space between the two devices. The two devices 2, 4 are spread apart a distance such that a space (between the two devices) in which an intrusion is to be detected is formed. Similar to the scenario of FIG. 6, the two devices are clock synchronized and calibrated. The main difference between the present scenario and the one shown in FIG. 6 lies in the lack of an accelerometer in the present scenario. An intrusion in the space comes as a disturbance or a change to values of the sets of time of flight. If a present time of flight value varies significantly from the previous time of flight value, an intrusion is said to have been detected. In another embodiment, the present system seeks the entry of a new, unknown signal into its monitored area (e.g., various types of signals such as transmissions from the phone of an intruder or the signal of a remote control device). It should be noted that the system may also use changes in the time of flight of signals to detect if there is movement in the room that does not cause a sensor to move.

Figure 9:
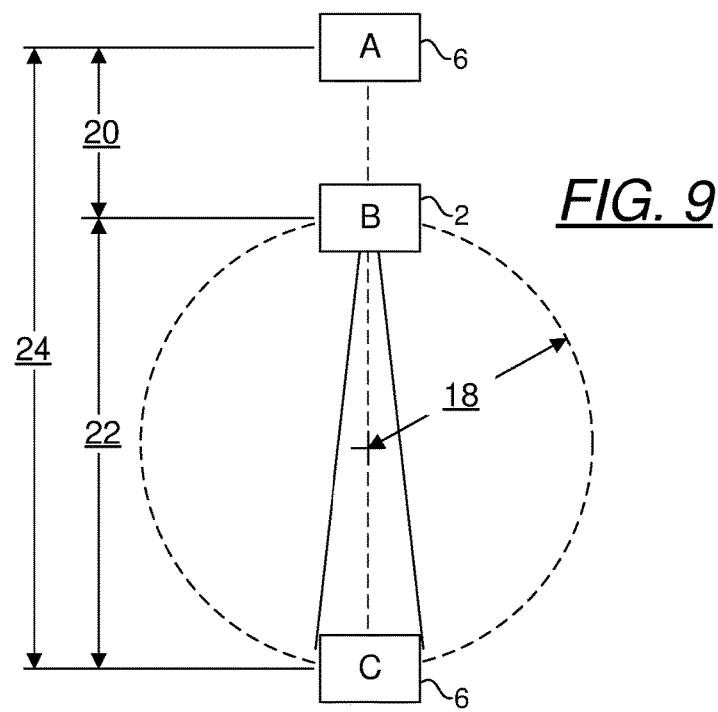
FIG. 9 is a diagram depicting an example of the use of a mesh network for communication between multiple devices or detection of one or more devices in a network.

FIG. 9 is a diagram depicting an example of the use of mesh network for communication between multiple devices or detection of one or more devices in a network. In this example, sensor A and mobile device case B are disposed at fixed locations at distance 20 apart and sensor C is mounted to an object configured to travel in a circular trajectory as shown in FIG. 9. The mobile device case B includes a directional antenna configured to detect an object in a direction coaxial to the direction from sensor A to mobile device case B. It is assumed that sensor A is not capable of directly detecting sensor C or providing a distance measurement between sensor A and sensor C, due to an obstruction or not having the same method of communication. It is further assumed that when sensor C comes within the field of view of the directional antenna, the mobile device case 2 will be capable of detecting the presence of sensor C. Therefore, although sensor A is not capable of detecting the presence of sensor C in the mesh network depicted in FIG. 9, the mobile device case 2 may relay location of sensor C relative to sensor A to sensor A if the radius 18 of sensor C trajectory is known. For example, in the positions shown, sensor A is disposed at a total distance 24 of distances 20 and 22. Distance 22 is twice radius 18. In an embodiment not shown, the mobile device case B may be replaced with a mobile device having a built-in antennae.

Figure 10:
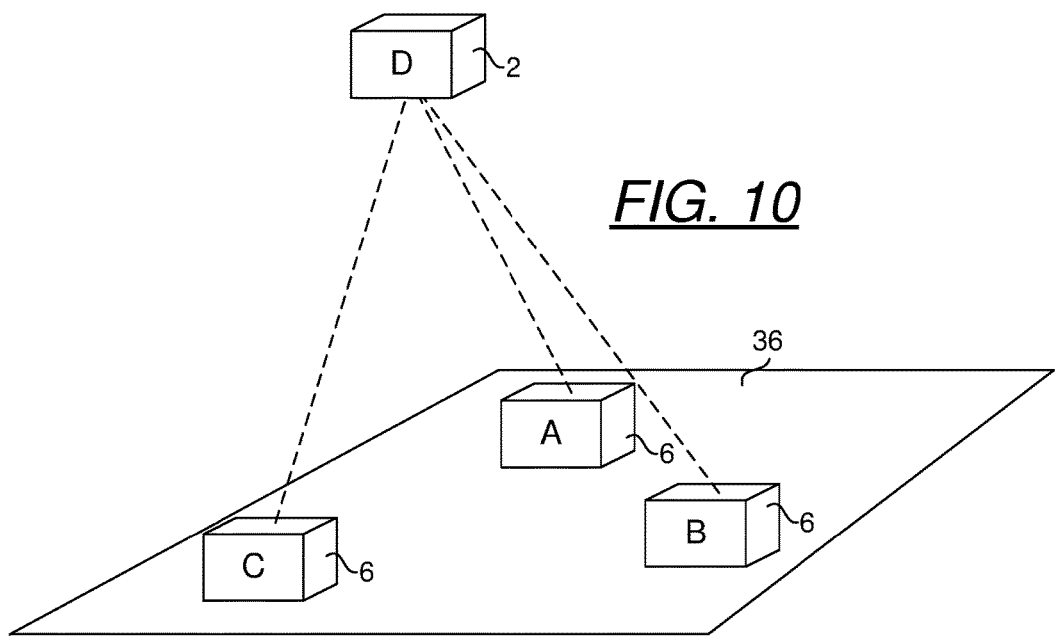
FIG. 10 is a diagram depicting an example of the use of a mesh network for locating a device.

FIG. 10 is a diagram depicting an example of the use of a mesh network for locating a device. In this example, sensors A, B and C are disposed at fixed known locations substantially upon a floor 36. The location of the mobile device case D, in relation to the sensors A, B and C, is to be determined by triangulation. Distances D-C, D-A and D-B are estimated based on the time of flight of signals communicated between each of the sensors A, B and C and the mobile device case 2. As there are two possible solutions, by placing the sensors A, B and C on the floor 36, the location of the mobile device case D relative to the sensors A, B and C can be estimated. The possible location of mobile device case D "under" the floor 36 as the other solution can be eliminated. Sensors A, B and C may alternatively be disposed at any location and not on a floor. If the signals communicated between the devices could travel through a floor, the strength of the signals may provide clue as to the proper solution as weak/problematic signals may indicate the second solution "under" the floor.

Figure 11:
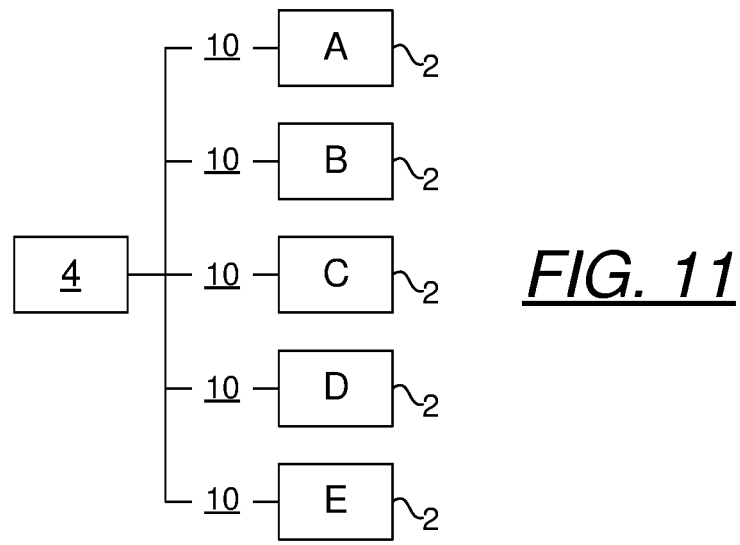
FIG. 11 is a block diagram depicting a mobile device, a plurality of mobile device cases and the relationships between these components.
Figure 12:
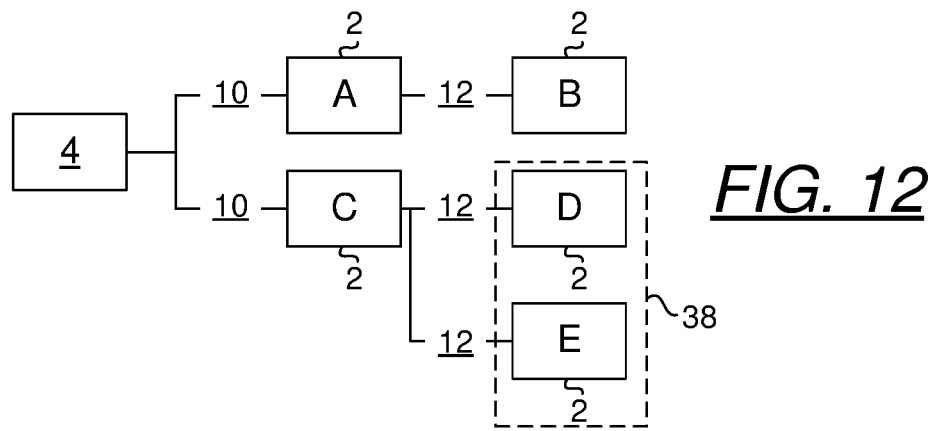
FIG. 12 is a block diagram depicting the components of FIG. 11 and functional connections between these components that are different than those disclosed in FIG. 11.
Figure 13:
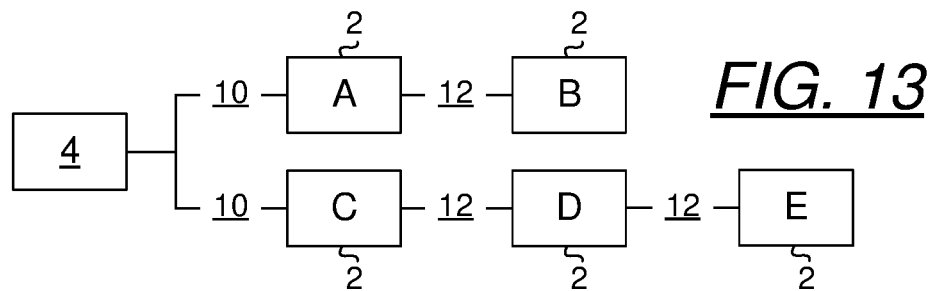
FIG. 13 is a block diagram depicting the components of FIG. 11 and functional connections between these components that are different than those disclosed in FIG. 11.

FIG. 11 is a block diagram depicting a mobile device 4, a plurality of mobile device cases and the relationships between these components. Each of the mobile device cases 2 is functionally connected directly to the mobile device 4. FIG. 12 is a block diagram depicting the components of FIG. 11 and functional connections between these components that are different than those disclosed in FIG. 11. In this mesh network, each of mobile device cases A and C is functionally connected directly to the mobile device 4. Mobile device case B is functionally connected to another mobile device case, i.e., mobile device case A. Each of mobile device cases D and E is functionally connected to another mobile device case, i.e., mobile device case C. In one aspect, it is possible to extend the range between mobile device 4 and a mobile device case 2 by functionally indirectly connecting a mobile device case (such as mobile device cases B, D and E) to the mobile device 4. In another aspect, mobile device cases 2 may alternatively be functionally grouped into one or more subgroups 38. A subgroup 38 can be viewed as a group where its constituents (e.g., mobile device cases D and E) functionally cooperate to yield a result that can then be relayed through at least one of the constituents to another component in the mesh network, e.g., the mobile device 4. For instance, if each of the mobile device cases D and E is equipped to take temperature readings, mobile device cases D and E may be configured to provide an average temperature reading based on the readings of mobile device cases D and E. FIG. 13 is a block diagram depicting the components of FIG. 11 and functional connections between these components that are different than those disclosed in FIG. 11. FIG. 13 depicts another possible means of forming a mesh network. In this example, mobile device case E is functionally connected to mobile device case D. In one embodiment, a subgroup is formed by bringing two components within the sphere of influence of each other and using a trigger, e.g., a button press to cause such relationship to be established. In another embodiment, a subgroup is formed by bringing components within the sphere of influence of each other such that a list of components present within the sphere of influence is visually presented and a selection can be made as to the components that form a subgroup.

Alternatively, the mobile device cases 2 of the examples depicted in FIGS. 11-13 may be replaced with sensors 6 and a mobile device case 2 may be used in place of the mobile device 4.

Figure 14:
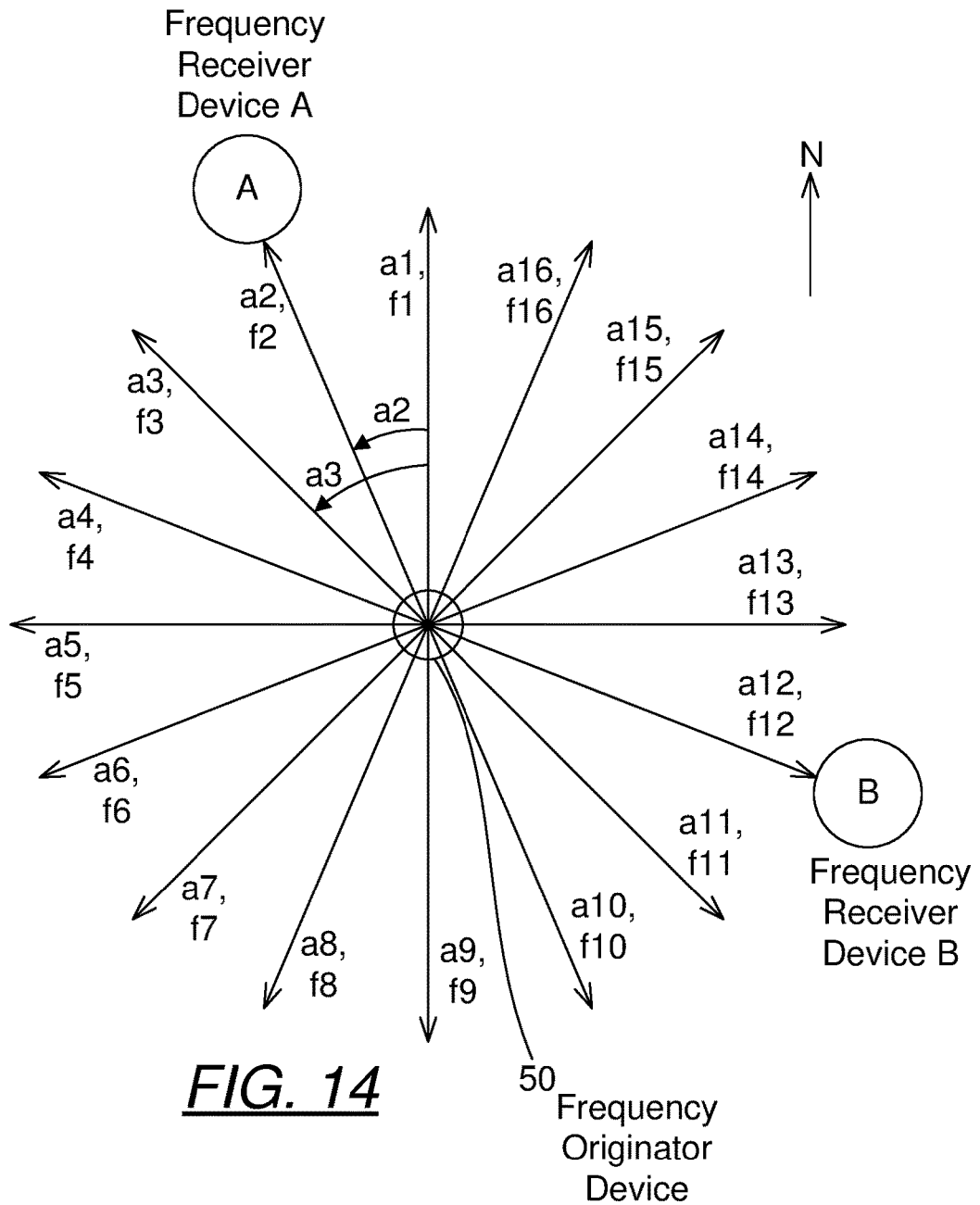
FIG. 14 is a diagram depicting one embodiment of a present localization system.

FIG. 14 is a diagram depicting one embodiment of a present localization system. In this embodiment, the location determination of a frequency receiver device (e.g., device A or B) is made based on the direction at which a signal or message is received from a frequency originator device. A frequency receiver device disclosed herein can be a mobile device already equipped with an on-board or built-in or external microphone, a device capable of receiving signals or messages transmitted as waves having a frequency response falling within or outside that of the frequency response of a typical microphone which ranges from about 20 Hz to about 20 kHz. A frequency receiver device which is said to have a frequency response of the typical range of frequencies can reproduce all frequencies within this range but not outside of this range. A frequency receiver device capable of a frequency response outside that of this range is adapted to reproduce frequencies outside of this range. A frequency originator device disclosed herein can be a broadcaster or any devices adapted to transmit signals or messages in waves having a frequency. In one embodiment, the frequency originator device 50 is a long range acoustic device (LRAD) which can be configured to broadcast signals of various frequencies at various orientations. In another embodiment, a phased array speaker system is used as the frequency originator device. Referring back to FIG. 14, at orientation a2, a signal having a frequency of f2 is broadcasted from LRAD. At orientation a12, a signal having a frequency of f12 is broadcasted from LRAD. Other signals of various other frequencies are broadcasted at their respective frequencies. At its depicted location, mobile device A (a frequency receiver device) is disposed at a location for receiving a signal at orientation a2 of frequency f2. In practice, LRAD can be a wave emitting device that is mounted on a rotary table such that it may be configured to emit signals of various frequencies at high speed depending on its orientation about its axis of rotation. Alternatively, multiple wave emitting devices may be disposed at different orientations instead, each configured to emit signals at a fixed frequency and pointed outwardly from a center. The latter is more robust as any delays due to the physical rotation of the wave emitting device as in the former will not occur. Each frequency originator device is programmed to emit a message in the direction the frequency originator device is disposed. Each message is therefore referred to as a directional message as only a frequency receiver device positioned within the field of influence of the directional message can receive this directional message.

In this embodiment, the cost of operating both the frequency originator device and the frequency receiver device is minimal. Most of the energy consumption of the present system lies in the broadcast of signals from the frequency originator device. When compared to a conventional localization device, e.g., a GPS system which not only requires external signals, e.g., those of satellites and relay stations but also may succumb to inclement weather, the present localization system utilizes smaller amounts of resources. There is neither satellite infrastructure nor any third party fees required in the present systems. The present systems are self-contained system without requiring external fees for signal information, e.g., GPS. The present systems can be readily used at low costs as they utilize existing communication means in sending alarms or danger notices, e.g., over an internet, data, or text, connection that would already be a part of the mobile device owners services. In the present systems, additional monitoring fees are not required to notify the authorities as the systems that can directly call the police through the mobile device, e.g., mobile phone. The energy consumption in the frequency receiver device is minimal as compared to other means of localization. The present systems utilize low energy consuming technology, e.g., sound frequencies and as a result, the devices in the systems do not need to be powered by large amounts of on-board battery power, reducing the battery costs which constitute a significant total cost portion in any mobile device. As the present systems are readily movable, they can travel easily with their owner from one location to another, relieving the need for multiple systems at multiple locations. In any systems disclosed herein, a speaker that is built-in or external to a mobile device can be used as a frequency originator device while a microphone that is built-in or external to the mobile device can be used as a frequency receiver device. As these components are typically already bundled with a mobile device, e.g., cell phone, no additional equipment or costs are required. In terms of the processors of the present systems, high volume or mass produced mobile devices such as a cell phone or tablet, etc., are readily equipped with such parts. Although a cell phone or tablet is used for other purposes, such as personal communication, etc., a cell phone or tablet is available at a much lower cost than a lower volume central processing unit for a security system due to economy of scale in the case of the cell phone or tablet. Compared to existing localization systems designed primarily for use in an outdoor, unobstructed environment, the present systems function by utilizing signals coming from devices already in the system or that have traveled together at the same time into an enclosed location. The present systems therefore do not rely on an existing infrastructure in the building to provide a signal source or data (e.g., they do not rely on a Wi-Fi being present).

In determining the location of a frequency receiver device with respect to a frequency originator device of a known location, the following steps are taken. First, the distance between the frequency receiver device and the frequency originator device is determined. In one embodiment, this is achieved by first synchronizing a clock of the frequency originator device with a clock of the frequency originator device. Then a directional message containing a broadcast time at which the directional message is broadcasted from the frequency originator device at an orientation about an axis of rotation of the frequency originator device and received by the frequency receiver device. The time of flight of the directional message is obtained by calculating the difference between a receive time at which the directional message is received by the frequency receiver device and the broadcast time. The distance between the frequency originator device and the frequency receiver device is determined by multiplying the time of flight of the directional message by the speed of the directional message. This is followed by determining the frequency of the directional message and determining the orientation of the directional message with respect to the frequency originator device by looking up a table containing orientations of messages about the frequency originator device with respect to the frequency of the messages. The location of the frequency receiver device can then be calculated based on the orientation of the directional message and the known location of the frequency originator device. It shall be noted that the known location is movable. In other words, it is the relative positioning of the frequency receiver device and the frequency originator device that is important. For example, in an application where a frequency receiver device is configured to follow a frequency originator device at a distance, the frequency originator device may be in a moving state at all times, but the frequency receiver device must move with the frequency originator device to maintain a preprogrammed distance.

Figure 15:
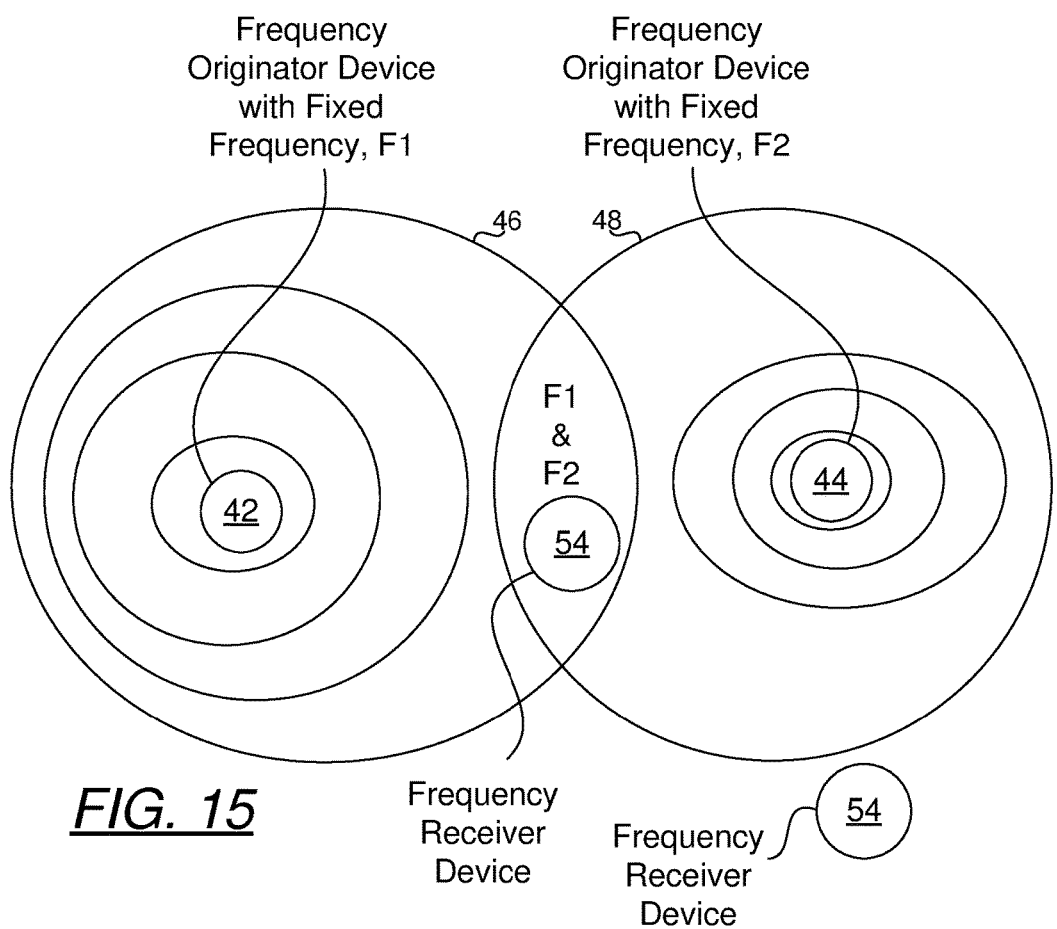
FIG. 15 is a diagram depicting another embodiment of a present localization system.
Figure 16:
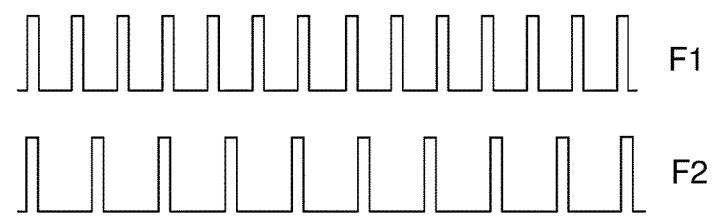
FIG. 16 is a diagram showing two different frequencies broadcasted using two different frequency originator devices as shown in FIG. 15.
Figure 17:
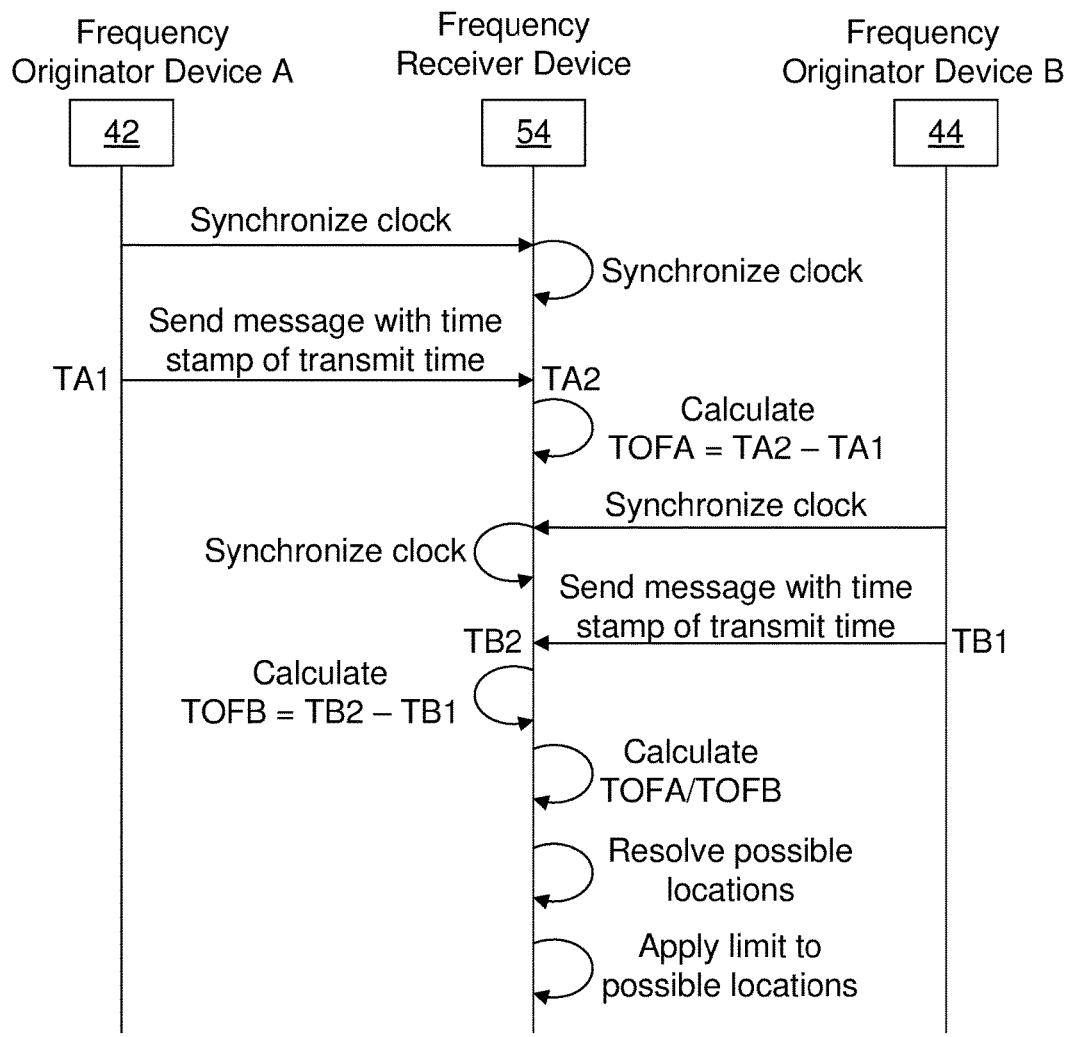
FIG. 17 is a sequence diagram depicting a means by which a device may be localized.
Figure 18:
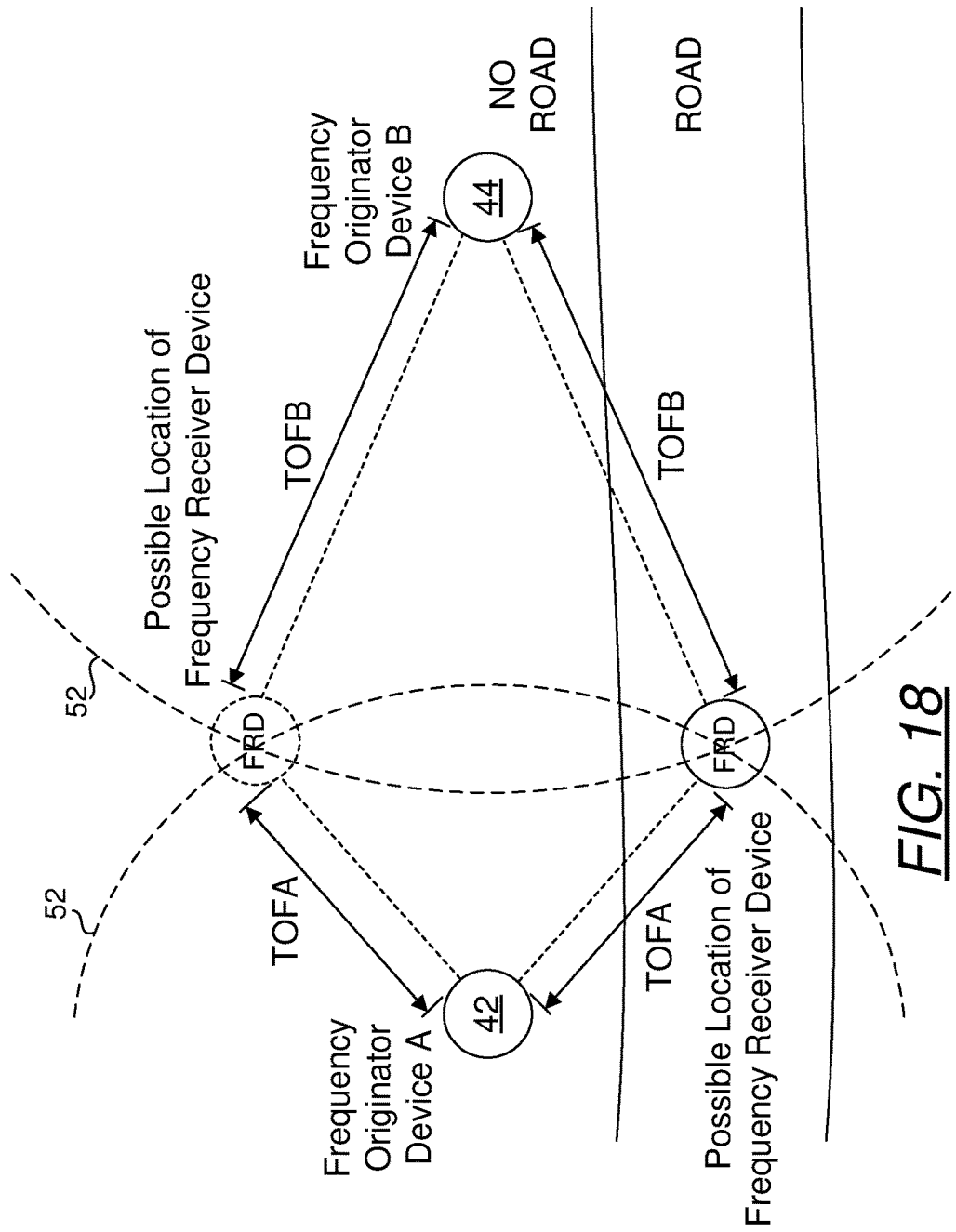
FIG. 18 is a plan view depicting a means by which localization is perfected with additional information.

FIG. 15 is a diagram depicting another embodiment of a present localization system. In this embodiment, two non-directional frequency originator devices are provided, each used to broadcast a signal or message having a fixed frequency, F1 or F2. FIG. 16 is a diagram showing signals or messages of two different frequencies broadcasted using two different frequency originator devices as shown in FIG. 16. Note the difference in wavelengths between the two messages. FIG. 17 is a sequence diagram depicting a means by which a device may be localized. FIG. 18 is a plan view depicting a means by which localization is perfected with additional information. In a two-dimensional space, a frequency receiver device may be said to assume one of the two possible locations as shown in FIG. 15. Referring to FIG. 18 and upon determining the distance of a frequency receiver device 54 from a frequency originator device using a method disclosed elsewhere herein, an arc 52 representing points equidistant from a frequency originator device can be disposed about the frequency originator device. In a two dimensional space, there exists two intersecting points, each representing a possible location of the frequency receiver device. In practice, a look-up table of the relative position of the frequency receiver device with respect to the ratio of the time of flight of messages 46, 48 (TOFA/TOFB) can be used to reduce real time computations in one or more controllers, e.g., one disposed in the frequency receiver device or one or both of the frequency originator devices of the localization system in resolving the location of the frequency receiver device given the locations of the frequency originator devices A and B. TOFA and TOFB represent the time of flight corresponding to the distances between the frequency receiver device and the frequency originator device A 42 and B 44, respectively.

The following steps are taken in determining the location of a frequency receiver device with respect to at least two frequency originator devices where the location of each is known. In the embodiment shown in FIG. 17, this is achieved by first synchronizing a clock of the frequency receiver device with a clock of one of the at least two frequency receiver devices. This is followed by receiving by the frequency receiver device, a message containing a broadcast time at which the message is broadcasted from the frequency originator device. Then a time of flight of the message is obtained by calculating the difference between a receive time at which the message is received by the frequency receiver device and the broadcast time. The above steps are repeated with a second frequency receiver device to result in a first time of flight, TOFA and a second time of flight, TOFB. A ratio of TOFA and TOFB is then calculated. Possible locations of the frequency receiver device are then resolved by looking up a table containing possible locations of the frequency receiver device with respect to the ratio of the first and second time of flight. The table is essentially a look-up table listing the TOFA/TOFB ratio with respect to the locations of the frequency receiver device relative to the locations of the frequency originator devices. As there are two possible solutions or locations in each two dimensional space as shown in FIG. 18, additional information is required to rule out one of the possible locations. At least one limit is applied to the possible locations to select one of the possible locations with high certainty. In the example shown in FIG. 18, frequency originator devices A and B are overlaid atop a map depicting a road. In this example, as it is assumed that the frequency receiver device is used for road navigation, the applied assumption or limit results in a plausible solution which points to the location of the frequency receiver device disposed on a road instead of a location where no roads exist. In another embodiment, the limit includes the time of flight results obtained from a third frequency originator device in a similar manner as in the case of the other two frequency originator devices. In this case, a unique solution exists which is disposed at a measured distance (or its corresponding time of flight) from frequency originator device A, a measured distance (or its corresponding time of flight) from frequency originator device B and a measured distance (or its corresponding time of flight) from the third frequency originator device in a two dimensional space. In order to obtain a unique solution in a three-dimensional space, a fourth frequency originator device will be required. In another embodiment, the limit includes the magnetization of a magnetic material, e.g., a ferromagnet, and the strength and/or direction of the magnetic field at a point in space as indicated by a magnetometer. The frequency originator devices may also be movable provided that the positional relationships between the frequency originator devices are known.

A frequency originator device can be a mobile device and whenever possible, it is preferably connected to a wall power source such that its service is uninterrupted. A frequency receiver device is preferably a mobile device such that its use is not tethered to a fixed location. The present localization method may be extended for use with venues already having frequency originator devices, e.g., stadiums, subways, malls, parking lots, etc.

Interference may occur during transmission of data from one device to another. In order to avoid interference, a strategy that determines the most favorable frequency of a signal is used. In doing so, signals are transmitted at varying frequencies from a frequency originator device to a frequency receiver device at, e.g., regular intervals. The signal with the shortest time of flight is considered to be the signal having most suitable signal frequency as signals received at a longer time of flight may indicate the presence of echoes or other effects of interference. Upon determining the most suitable signal frequency, future communications between the frequency originator device and the frequency receiver device will then be made at this frequency to avoid interferences.

The present systems are also capable of use underwater where GPS is unavailable. When used underwater, suitable water-proofing technologies shall be used to ensure readily available mobile devices which are typically designed for use in air do not get water intrusions.

Figure 19:
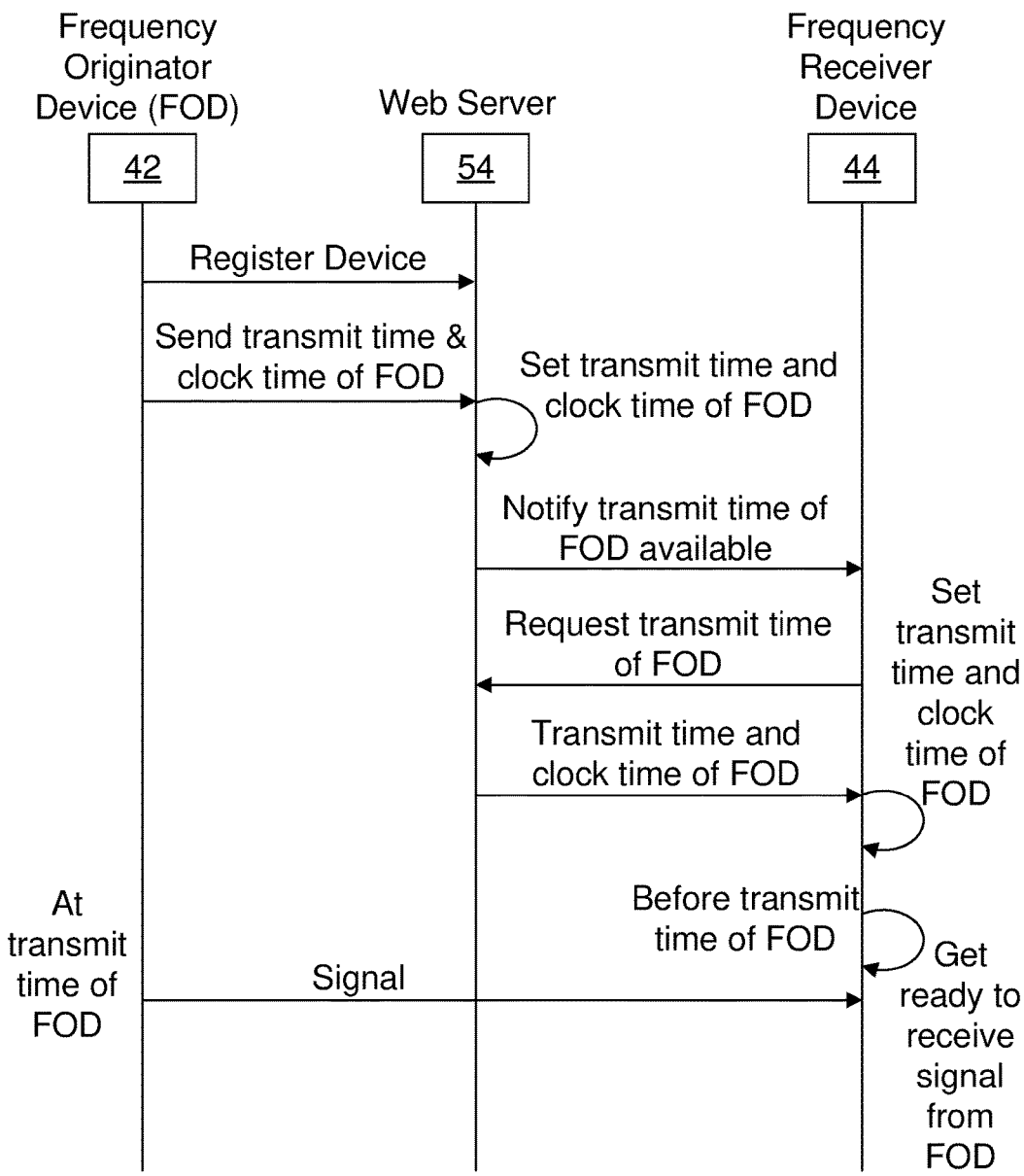
FIG. 19 is a sequence diagram depicting a means by which two devices are clock time synchronized via a web server.

FIG. 19 is a sequence diagram depicting a means by which two devices are clock time synchronized via a web server. In this example, one of the devices is a frequency originator device and the other, a frequency receiver device. Each of the frequency originator device and frequency receiver device can be a mobile device or a fixed device. The frequency originator device is first registered with a web server with some form of identification. A transmit time (the time at which a signal is to be broadcasted by the frequency originator device) is then sent to the web server where the transmit time is then associated with this frequency originator device. The web server is configured to notify the frequency receiver device that a frequency originator device is ready to make a signal broadcast. As the frequency receiver device is interested in receiving the broadcast, it responds by sending a request to the web server for the transmit time and clock time of the frequency originator device. Such information is sent to the frequency receiver device. Upon receiving such information, the transmit time and clock time are saved and used to set appropriate functions to anticipate the arrival of a signal from the frequency originator device. It shall be noted that the clock time is a time stamp in which latencies due to transmissions of this information from the frequency originator device to the frequency receiver device has been considered. The frequency receiver device is then put in a ready and standby state prior to the transmit time of the signal such that upon the arrival of the signal, the frequency receiver device is ready to receive and process the signal.

Figure 20:
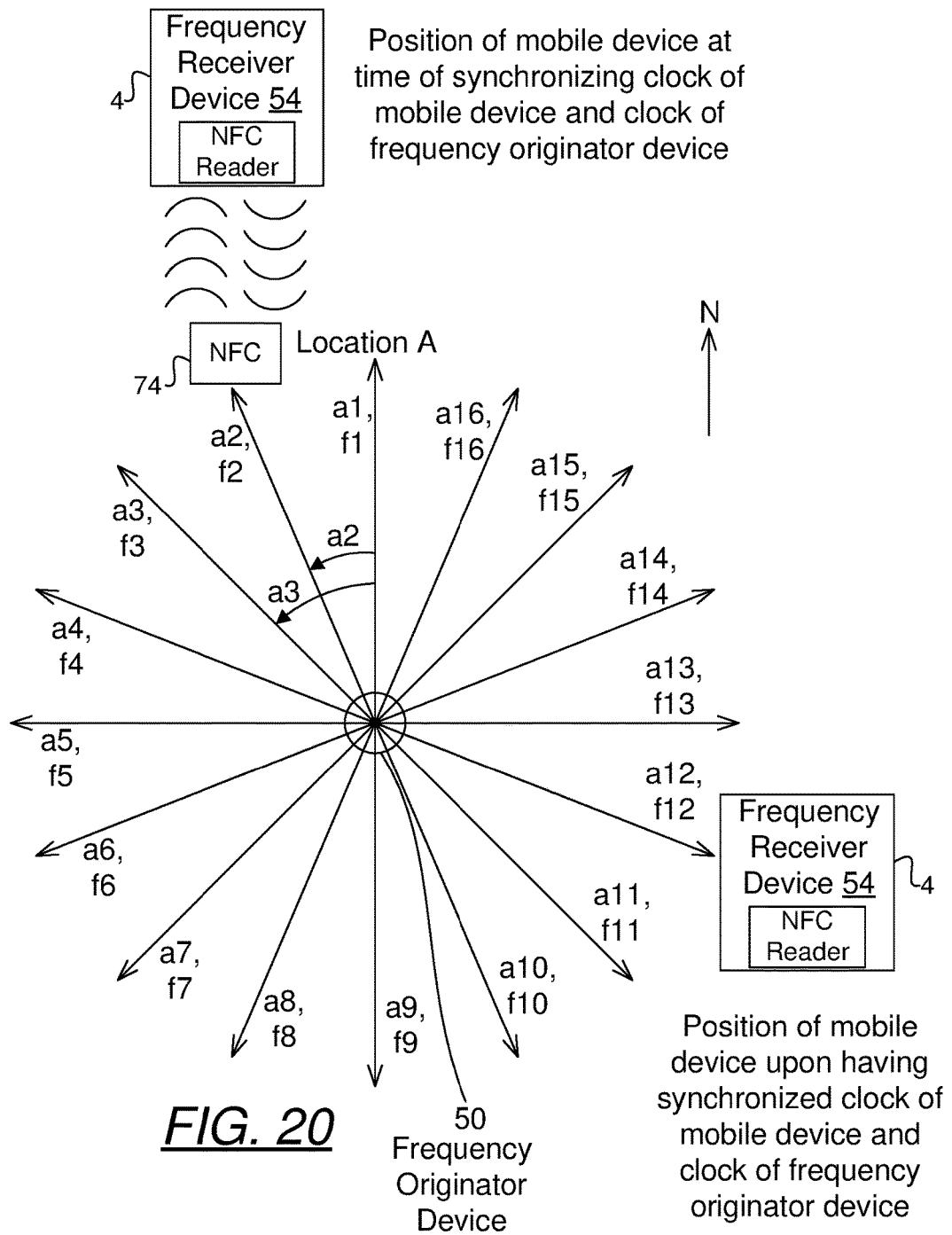
FIG. 20 is a diagram depicting one embodiment of a present localization system including the use of an information storage device.
Figure 21:
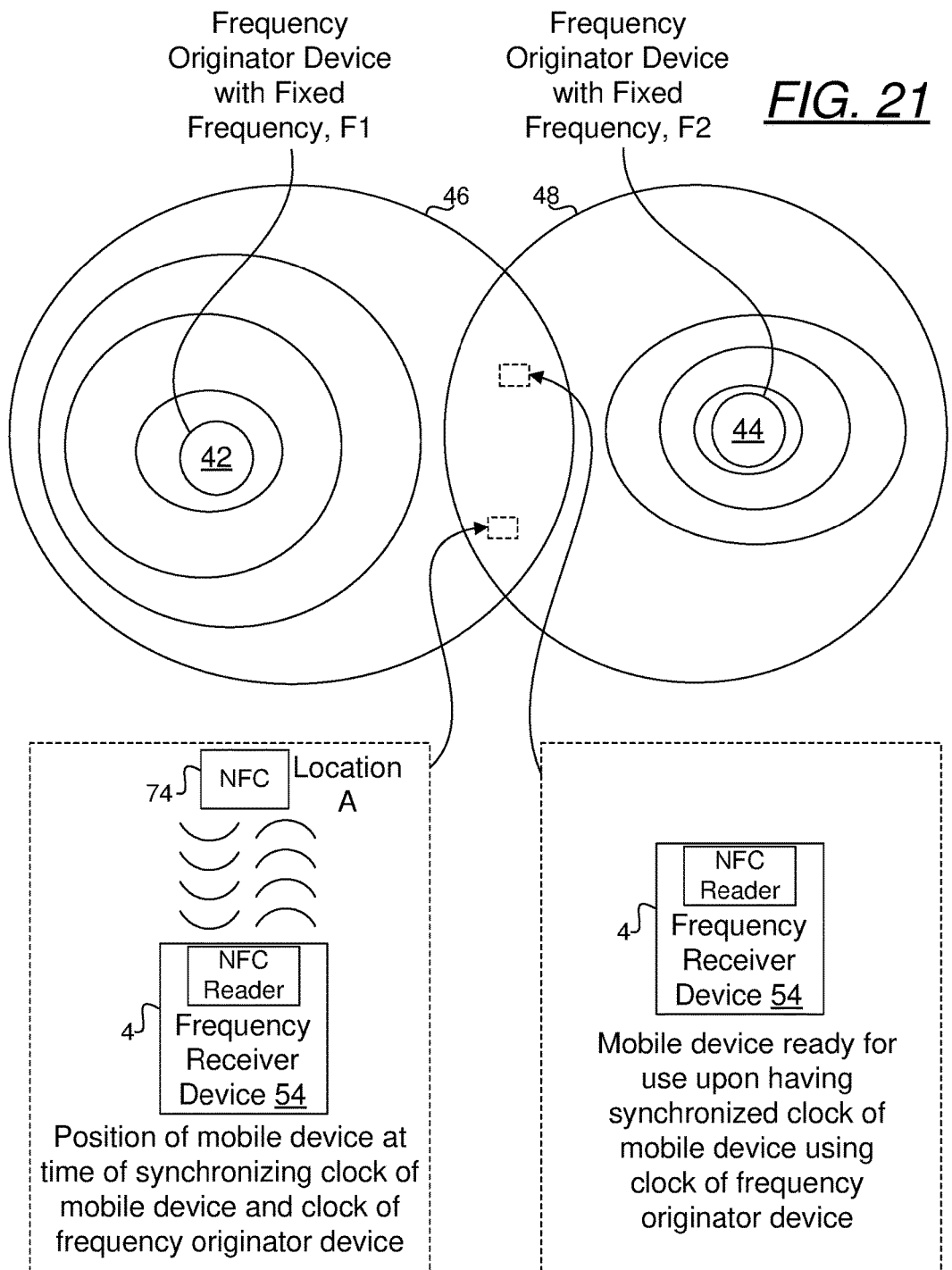
FIG. 21 is a diagram depicting another embodiment of a present localization system including the use of an information storage device.

FIG. 20 is a diagram depicting one embodiment of a present localization system including the use of an information storage device 74. FIG. 21 is a diagram depicting another embodiment of a present localization system including the use of an information storage device. In one example, a frequency originator device or a frequency receiver device is a stand-alone device which includes its own controller and is not coupled with a mobile device. In another example, a frequency originator device or a frequency receiver device is coupled to a mobile device, e.g., cell phone, electronic pad, etc. In the latter example, computations and other processing activities required by the frequency originator and receiver devices may be made in the mobile device, removing the need to require separate controllers in the frequency originator and receiver devices. In the configurations shown in FIGS. 14 and 15, clock synchronizing of the frequency receiver device by the frequency originator device may be performed by communicating the clock time of one device (frequency originator device or frequency receiver device) to another, via, e.g., the internet. In cases where no such communication is available or desired to either one or both of the devices, clock synchronizing is made possible by the following process. The distance between a frequency originator device and a frequency receiver device is first predetermined and stored in an information storage device 74 along with the carrier frequency of the frequency originator device. A time correction 70 is then calculated from a message received by the frequency receiver device from the frequency originator device based on the transmit time of the message that is embedded in the message and the TOF that is calculated based on the distance between the frequency originator device and the frequency receiver device and the speed of transmission of the message. In one embodiment, the information storage device 74 is a short-range Radio Frequency Identification (RFID) tag. In one embodiment, the RFID tag is a Near Field Communication (NFC) tag. An NFC tag is preferred as it is unpowered, does not require contact with its reader to function and yet it requires that its reader to be placed in close proximity to function, thereby indicating that when disposed in close proximity to a reader, the reader's location is essentially the NFC's location. Disclosed herein is a localization system where the location of a frequency receiver device is first obtained, similar to the manner in which a location is obtained for each of frequency receiver devices A and B shown in FIG. 14 and the frequency receiver devices shown in FIG. 15. Referring to FIG. 20, as the carrier frequency of messages is programmed to vary according to the angle at which the messages are broadcasted, the location of the frequency receiver device relative to the frequency originator device can be determined based on the carrier frequency at which messages are received by the frequency receiver device and the distance of between the frequency originator device and the frequency receiver device. As NFC is a very short range contactless data transfer technology, the placement of an NFC tag at a location previously associated with a frequency receiver device as identified using a frequency originator device-frequency receiver device pair as shown in FIGS. 14 and 15, provides a close approximation of the NFC tag's location. In this example, a NFC tag is disposed at location A. The use of an NFC tag removes the reliance on other means for accessing information, i.e., via the internet regarding the carrier frequency or a range of carrier frequencies of messages transmitted from the frequency originator device and distance between the frequency originator device and the frequency receiver device or the NFC tag which is now placed in place of a frequency receiver device which was used to identify such distance. Such information is instead stored in the NFC tag. In use, a passerby or user armed with an NFC reader, can bring the reader in the vicinity of NFC tag to within range, e.g., about 4 cm, to initiate a handshake and obtain the information stored in the NFC tag.

Figure 22:
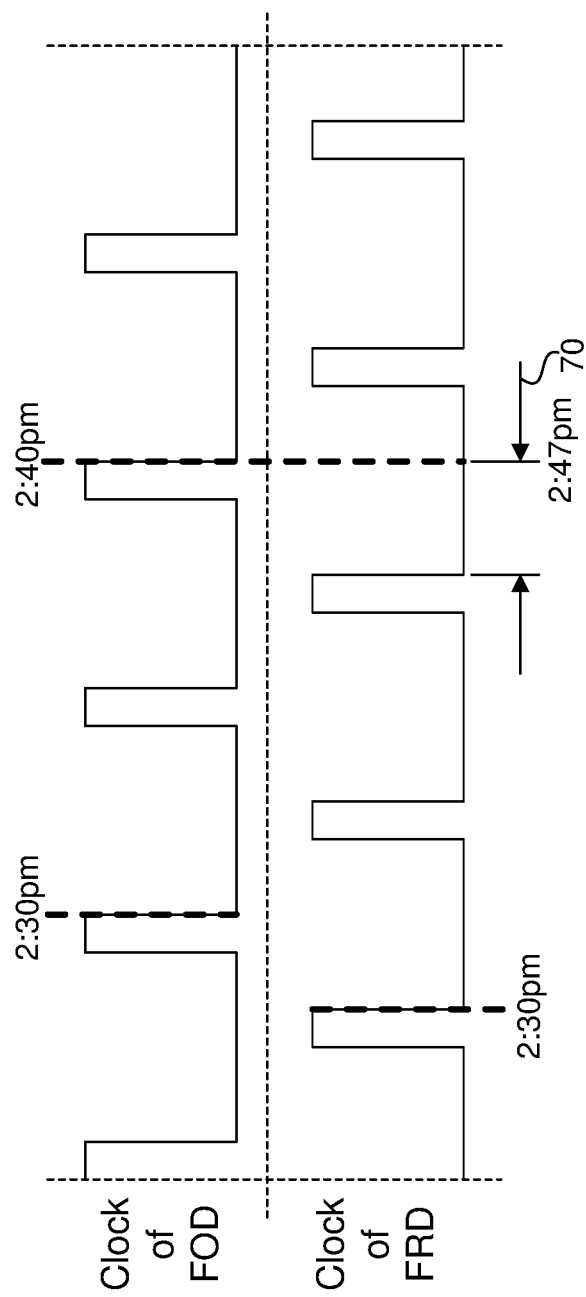
FIG. 22 is a diagram depicting an example of a correction that is required to be made to synchronize the clock of a frequency originator device and a frequency receiver device.

Armed with the distance d and a known speed s for the traversal of messages sent from the frequency originator device to the frequency receiver device, a TOF can be calculated e.g., via communications tool or application already built into or that is otherwise available on a mobile device, e.g., cell phone, to which the NFC reader is functionally connected, according to the equation s=d/TOF or TOF=d/s where d=distance between the frequency originator device and the NFC tag and s represents the speed of a message traversing the distance between the frequency originator device and the NFC tag or if sound waves are used, s is a known value or s=speed of sound. Upon obtaining the TOF, a time correction for the frequency receiver device can be calculated as follows. When a message is determined to be of a carrier frequency the same as that specified by the NFC tag, the frequency receiver device is set to receive it and proceeds to process it. The message which is believed to be originating from the frequency originator device contains the clock time t1 at which the message started to get transmitted from the frequency originator device. Assume T2 is the clock time at which the frequency receiver device received the message. The frequency originator device's clock time at the time the frequency receiver device received the message is t1+TOF. Therefore, the frequency originator device's clock time and the frequency receiver device's clock time differs by a time correction of (T2−(t1+TOF)). FIG. 22 is a diagram depicting an example of a time correction that is required to be made to synchronize the clock of a frequency originator device and a frequency receiver device. For instance, as shown in FIG. 22, at any moment, the clock time of the frequency originator device differs from the clock time of the frequency receiver device by a correction amount, e.g., 7 minutes (or 420 seconds) in this case. Once a time correction has been obtained, the frequency receiver device can be used to indicate its location. A user carrying the frequency receiver device can then be moved around an area within the transmission range of the frequency originator device and be tracked using the frequency originator device. For instance, if a message is starting to be transmitted from the frequency originator device at the frequency originator device's clock time of t3 and received at the frequency receiver device's clock time of T4, the TOF of the message can be obtained by subtracting t3 from T4 with the time correction applied or TOF=T4−t3+time correction. If more than one frequency originator device is used, additional NFC tags may be used, each storing a set of information pertinent to one frequency originator device. Alternatively, all necessary clock time synchronizing information for all frequency originator devices in one area is contained within only one NFC tag. For users' convenience, multiple NFC tags may be disposed at various locations provided each has been stored pertinent information for the particular locations the NFC tags have been placed. When NFC tags are used to store information pertaining to the carrier frequency and distance to the frequency originator device, no access of such information is necessary via the internet. In another embodiment, each NFC contains a Universal Resource Identifier (URI) where the carrier frequency and distance to its corresponding frequency originator device are accessed via the URI. In a cell phone-equipped frequency receiver device, the access to an information storage may also be identified by a URI and accessed via a cellular network.

Figure 23:
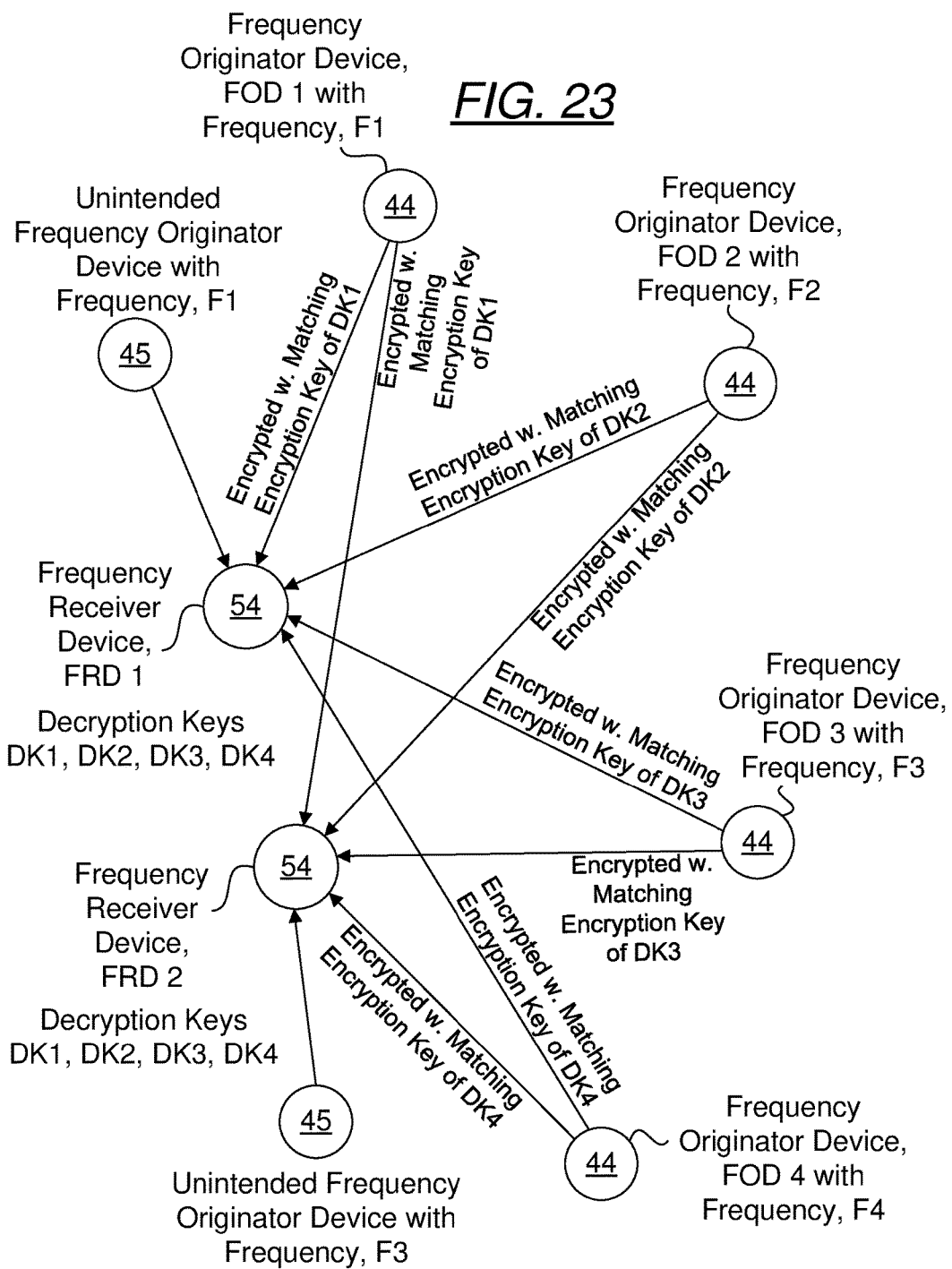
FIG. 23 is a diagram depicting the use of encryption in one embodiment of a present localization system.

FIG. 23 is a diagram depicting the use of encryption in one embodiment of a present localization system. Although encryption is shown for only the configuration of FIG. 23, it is applicable to any configurations involving the broadcast of a message from a frequency originator device where the message is then received in a frequency receiver device. In this example, a system having four frequency originator devices 44, each broadcasting messages at a unique carrier frequency, e.g., F1 for frequency originator device (FOD) 1, F2 for FOD 2, F3 for FOD 3 and F4 for FOD 4, are shown to broadcast messages subsequently received by two frequency receiver devices 54, i.e., frequency receiver device (FRD) 1 and FRD 2. Two unintended frequency originator devices are shown. Unintended frequency originator devices can be any devices broadcasting messages either as a result of a naturally occurring action or a deliberate action meant to interrupt or sabotage the use such a system to determine locations of frequency receiver devices. Unintended FODs 45 may be present within the localization system shown in FIG. 23 where such FODs may broadcast messages of carrier frequencies expected by FRDs. In a non-encrypted system, the use of a common carrier frequency can cause one or more frequency receiver devices 54 to pick up messages broadcasted by the unintended FODs 45 if these FODs are placed within the transmission range of the frequency originator devices. In one embodiment, prior to transmitting a message, it is first encrypted with an encryption key in the frequency originator device 44. A decryption key DK1, DK2, DK3, DK4 is made available to the frequency receiver devices 54 via communication means, e.g., the internet from a server, retrieving such information from an information storage device or such information may simply be preprogrammed in the frequency receiver device or made available to an information storage device, e.g., an NFC tag. Upon receipt of a message, it is decrypted using the decryption key DK1, DK2, DK3, DK4. Messages from the unintended frequency originator devices 45 may be received as their carrier frequencies may match those of the expected frequencies. However, no instructions will be available for decrypting the messages. Therefore, the messages will be ignored. It shall therefore be apparent that the present mechanism can be used to ignore irrelevant data.

Figure 24:
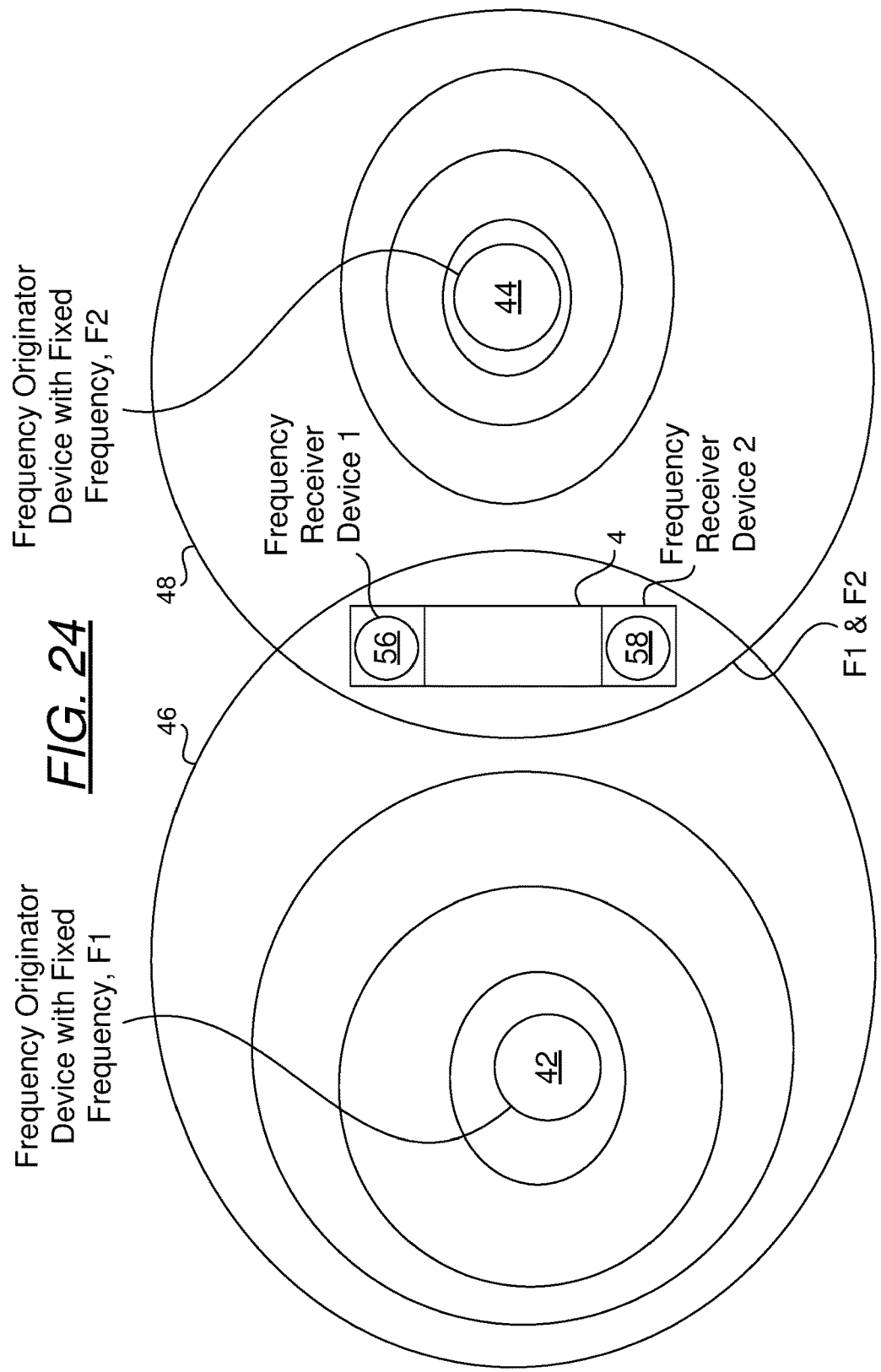
FIG. 24 is a diagram depicting another embodiment of a present localization system including the use of more than one frequency receiver device on a single mobile device.
Figure 25:
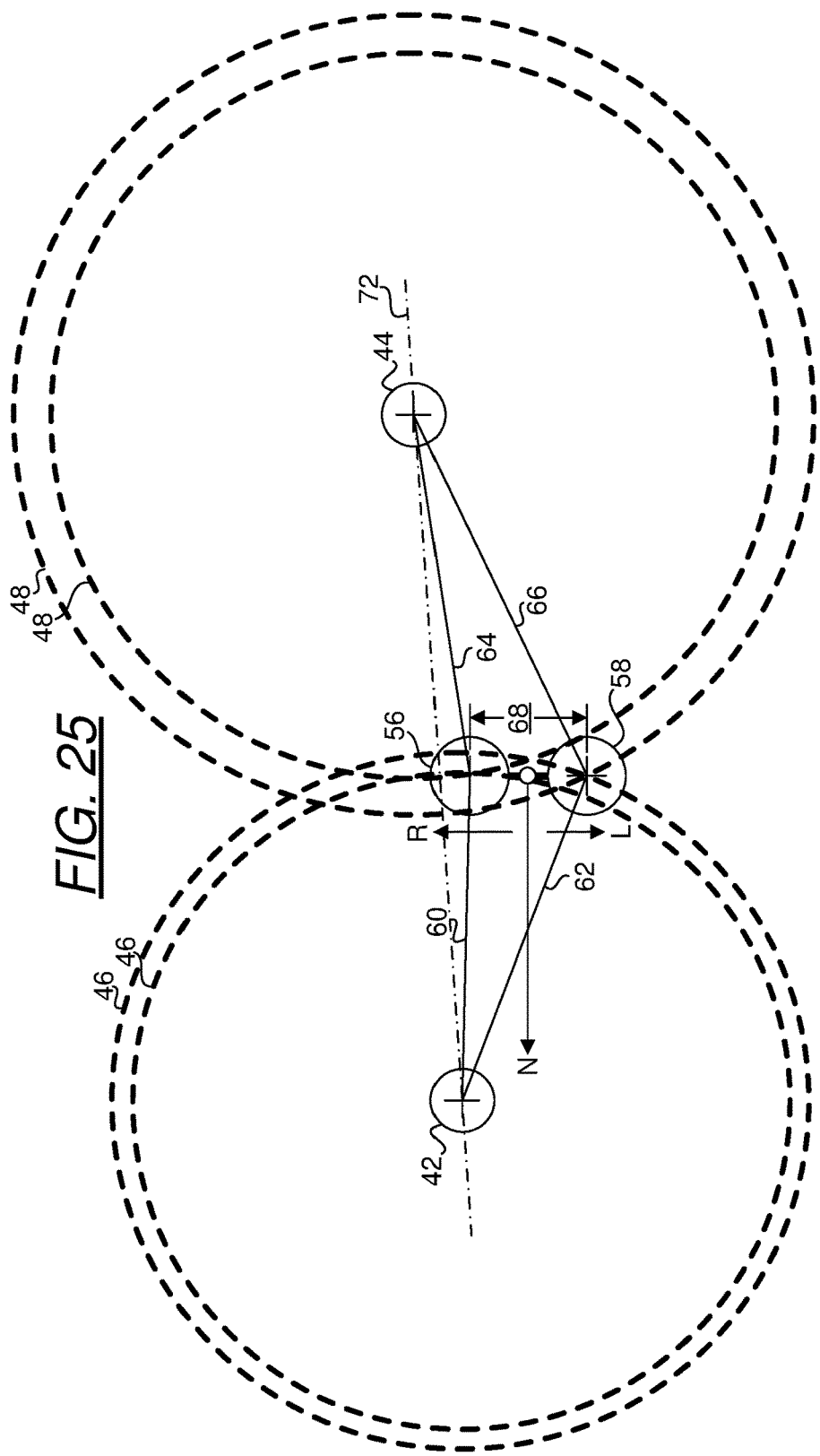
FIG. 25 is a diagram showing the embodiment of FIG. 24 depicted with distances between frequency originator and receiver devices shown where such distances can be used to uniquely identify the location of the mobile device upon which the frequency receiver devices are attached.
Figure 26:
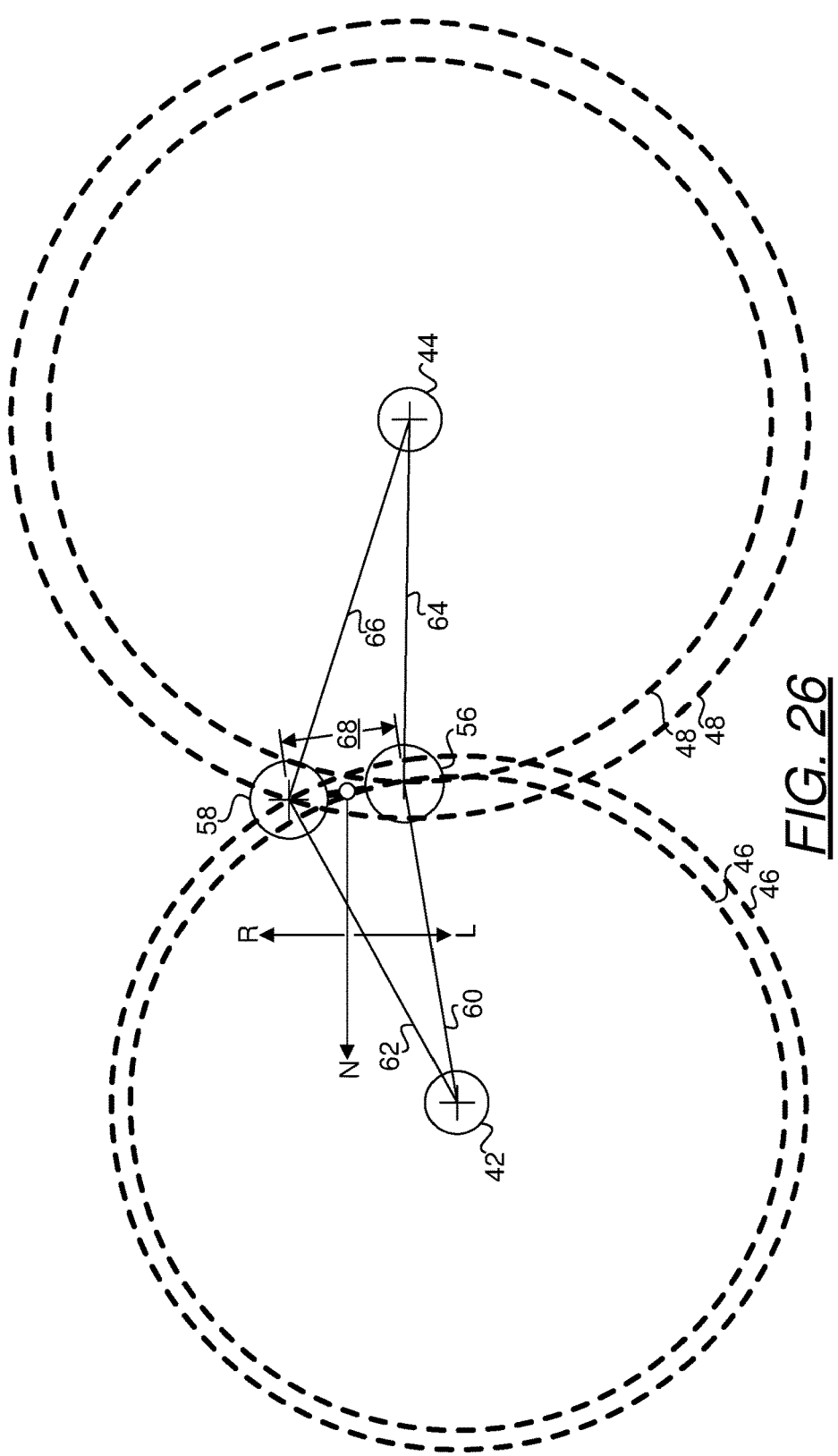
FIG. 26 is a diagram possible location of the mobile device of FIG. 25 where such possible location is eliminated by having the heading information shown in FIG. 25.

FIG. 24 is a diagram depicting another embodiment of a present localization system including the use of more than one frequency receiver device on a single mobile device 4. FIG. 25 is a diagram showing the embodiment of FIG. 24 depicted with distances between frequency originator 42, 44 and receiver 56, 58 devices shown where such distances can be used to uniquely identify the location of the mobile device 4 upon which the frequency receiver devices 56, 58 are functionally coupled. FIG. 26 is a diagram of a possible location of the mobile device of FIG. 25 where such possible location is eliminated by having the heading information shown in FIG. 25. In this embodiment, in identifying the location of the mobile device 4, it is equipped with more than one frequency receiver devices 56, 58. Only two frequency originator devices 42, 44 of known locations are required. The mobile device 4 to which each frequency receiver device 56, 58 is attached further includes a heading indicating device, e.g., magnetometer, gyrocompass etc., to further provide heading information. In one embodiment, the magnetometer is further functionally coupled with a gyroscope to remove a requirement that mobile device 4 be placed in a particular orientation so as to function properly, making it orientation-agnostic. No additional information is required, e.g., as shown in FIG. 18, to perfect the localization of the singly disposed frequency receiver devices. In one embodiment, the heading indicating device is disposed in a manner that it is physically located between the two frequency receiver devices 56, 58 as shown in FIG. 25. A pattern can be established that, in order for the distances 60, 62, 64, 66 to be disposed in the configuration shown in FIG. 25, the mobile device 4 must be disposed in a unique orientation, i.e., in the orientation shown in FIG. 25. A unique solution to the location of mobile device 4 is possible as it can be determined on which side a TOF has been collected. For instance, the TOF corresponding to distance 60 or the frequency receiver device 56 is disposed on the right side of north heading and the TOF corresponding to distance 62 or the frequency receiver device 58 is disposed on the left side of north heading. Without the heading information, it is possible that the location of the frequency receiver devices 56, 58 can be located in positions shown in FIG. 26. It is also possible that the positions of the frequency receiver devices 56, 58 can be two points in a plane traced when the two points are revolved around axis 72. With the heading information however, there can only be one solution which meets the requirements of the distances 60, 62, 64, 66. It therefore would not have been possible to have the TOFs disposed in a configuration as shown in FIG. 26, making the solution shown in FIG. 25 unique. With two frequency receiver devices 56, 58 disposed at detected distances 60, 62 from the first originator device 42 and detected distances 64, 66 from the second originator device 44, the availability of a heading indicating device enables possible locations of the mobile device 4 to be eliminated. In one embodiment, a frequency originator device 42, 44 is a music box, such as the one disclosed in U.S. Pat. No. 5,449,856 to Nakamori.

In one instance, the localization methods disclosed elsewhere herein is applicable to a system for guiding a vehicle without the use of a Global Positioning System (GPS). The absolute location of a frequency receiver device can be determined when it is functionally coupled to at least three frequency originator devices positioned at known locations as shown elsewhere herein. However, armed with an additional device, e.g., a magnetometer, as disclosed elsewhere herein, the location of a frequency receiver device may be determined or inferred when the frequency receiver device is only functionally coupled with one or two frequency originator devices positioned at known locations. Under ideal conditions, a planned path of a vehicle may be executed according to planned way points. However, two conditions can occur, each of which requires that the frequency receiver device be frequency calibrated such that it can be clock synchronized to one or more frequency originator devices according to a method disclosed elsewhere herein. First, a frequency drift, defined as an unintended and generally arbitrary offset of an oscillator from its nominal frequency, can occur. Causes may include component aging, changes in temperature that alter the piezoelectric effect in a crystal oscillator, or problems with a voltage regulator which controls the bias voltage to the oscillator. Second, a frequency receiver device is required to clock synchronize with one or frequency originator devices whose influence the frequency receiver device is about to enter. Disclosed herein is a method for calibrating a frequency receiver device to enable it to be engaged with or continue to be functionally engaged with one or more frequency originator devices.

Figure 27:
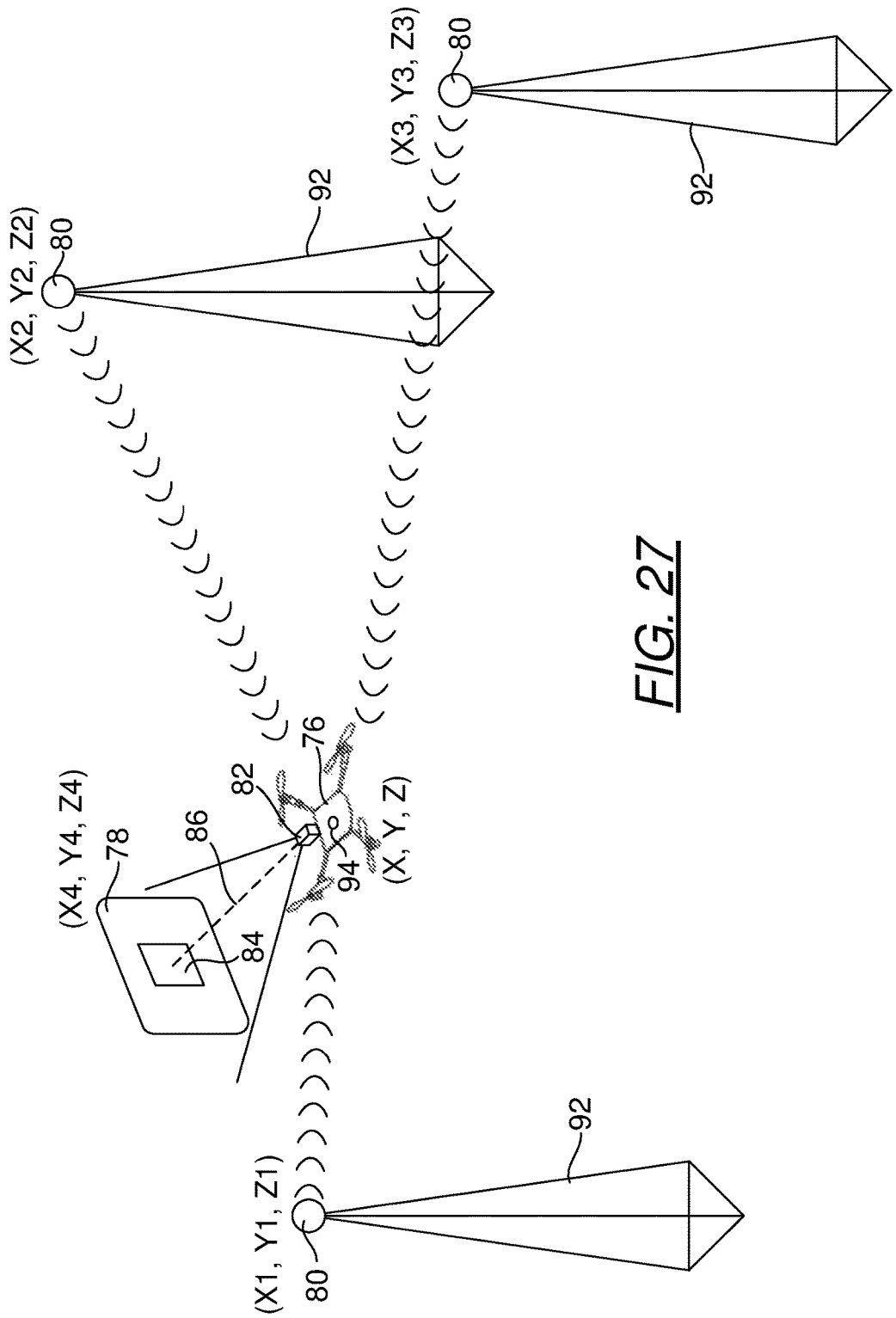
FIG. 27 is a diagram depicting a frequency calibration mechanism for identifying the signals a frequency receiver device is configured to receive in an environment containing three frequency originator devices.

FIG. 27 is a diagram depicting a frequency calibration mechanism for identifying the signals a frequency receiver device is configured to receive in an environment containing three frequency originator devices 80. In this example, each frequency originator device 80 may be supported on a tower 92 such that broadcasts from the frequency originator device 80 may be free from obstructions. The frequency receiver device 94 that is disposed on a vehicle, e.g., an aerial drone 76, is clock synchronized with all three frequency originator devices 80 and as the location of each frequency originator device, i.e., (X1, Y1, Z1), (X2, Y2, Z2) and (X3, Y3, Z3), is known and the location of the frequency receiver device 94 can be calculated, where X, Y and Z components represent the coordinates of the frequency originator devices 80. If provided a planned path, the vehicle 76, can be driven from one way point to the next while functionally engaged with the frequency originator devices 80. The vehicle 76 is further equipped with an image acquisition device 82, e.g., camera for receiving image inputs from its surroundings. For purposes of expediency, a rotary scanning camera may be used as such a device would allow the camera to capture images in a wide range of angles with respect to the direction of movement of the vehicle 76 and increases the likelihood that a visually unique object can be detected. The location of the frequency receiver device 94 can then be determined based on the captured images if a visually unique object has been identified as its location is known and a relative location of the frequency receiver device from the visually unique object can readily be calculated, in one instance, based on the focal length of the image acquisition device 82, the known height of the visually unique object 78, the image height, the height of the visually unique pattern 84 as it appears in the captured image and the height of the sensor of the image acquisition device 82. In one embodiment, a lookup table is constructed and made available for access for the present calibration method to function. The lookup table correlates a plurality of pre-determined visually unique patterns with various parameters. In one embodiment, each visually unique pattern is correlated with parameters including a corresponding pre-determined known location of the visually unique pattern, at least one corresponding pre-determined broadcast frequency of at least one pre-determined frequency originator device with a corresponding pre-determined known location. The lookup table enables the identification of one or more frequency originator devices that are configured to be functionally coupled to the frequency receiver device. For instance, if the location of the visually unique pattern can be obtained from the lookup table and the relative location of the frequency receiver device can be calculated based on an image of the visually unique pattern as captured from the frequency receiver device, the location of the frequency receiver device can be determined. The location of a frequency originator device that is configured to be functionally coupled to the frequency receiver device and as identified in the lookup table can be obtained directly from the lookup table. For instance, the locations of target frequency originator devices at (X1, Y1, Z1), (X2, Y2, Z2) and (X3, Y3, Z3) as shown in FIG. 27 would be entered in the lookup table such that they can be accessed. The distance between the frequency receiver device and each target frequency device can then be determined as the location of each of these devices is now known. Armed with this distance and the broadcast frequency of the target frequency originator device which is obtained directly from the lookup table, the frequency receiver device can now be clock synchronized with the target frequency originator device according the clock synchronization method disclosed elsewhere herein.

It can now be summarized that a frequency receiver device can be calibrated in the following manner. An image of a visually unique object having a visually unique pattern is first obtained where the location of the visually unique object and hence the visually unique pattern, is known. The image is checked against a database of landmarks or known patterns to see whether a landmark or a known pattern has been detected by comparing the visually unique pattern to a list of pre-determined visually unique patterns. Algorithms for picking out visually unique patterns from images have been widely available and do not constitute the subject of the present invention. Upon detecting a match, a relative location of the frequency receiver device from the visually unique pattern is determined based on information including the visually unique pattern. A new broadcast frequency of a frequency originator device is determined from a lookup table correlating a plurality of pre-determined visually unique patterns, their corresponding pre-determined known locations and corresponding pre-determined broadcast frequencies of corresponding pre-determined known locations of frequency originator devices. The location of the frequency receiver device is subsequently determined from the frequency originator device based on the relative location of the frequency receiver device from the pre-determined known location of the visually unique pattern. Algorithms for determining a relative location of an image acquisition device with respect to an object using an image of the object have been widely available and do not constitute the subject of the present invention. A clock of the frequency receiver device is then synchronized to a clock of the frequency originator device based on the new frequency of the frequency originator device and the distance between the frequency receiver device and the frequency originator device. Upon synchronization, the frequency receiver device is now capable of determining its own location on the concept of TOF disclosed elsewhere herein. The localization capability can then be applied to the navigation of a vehicle if the frequency receiver device is physically associated the vehicle.

In one embodiment, a visually unique object or pattern is three-dimensional. In one embodiment, a visually unique pattern is associated with one or more instructions for instructing a vehicle in continuing to investigate the visually unique pattern until it can be ascertained that the visually unique pattern is one which is listed in the lookup table for pertinent information for calibration of the frequency receiver device. In one instance, a visually unique object is three-dimensional and four-sided with each side providing further instructions on how the visually unique pattern is to be verified. For example, a vehicle comes from the south and detects a visually unique pattern, and subsequently going to the east as it is instructed upon detecting a first part (i.e., as viewed from the south) of the visually unique pattern. The vehicle may be instructed to investigate yet another side of the visually unique pattern or the visually unique pattern may be considered verified upon detecting the patterns of the two sides.

Figure 28:
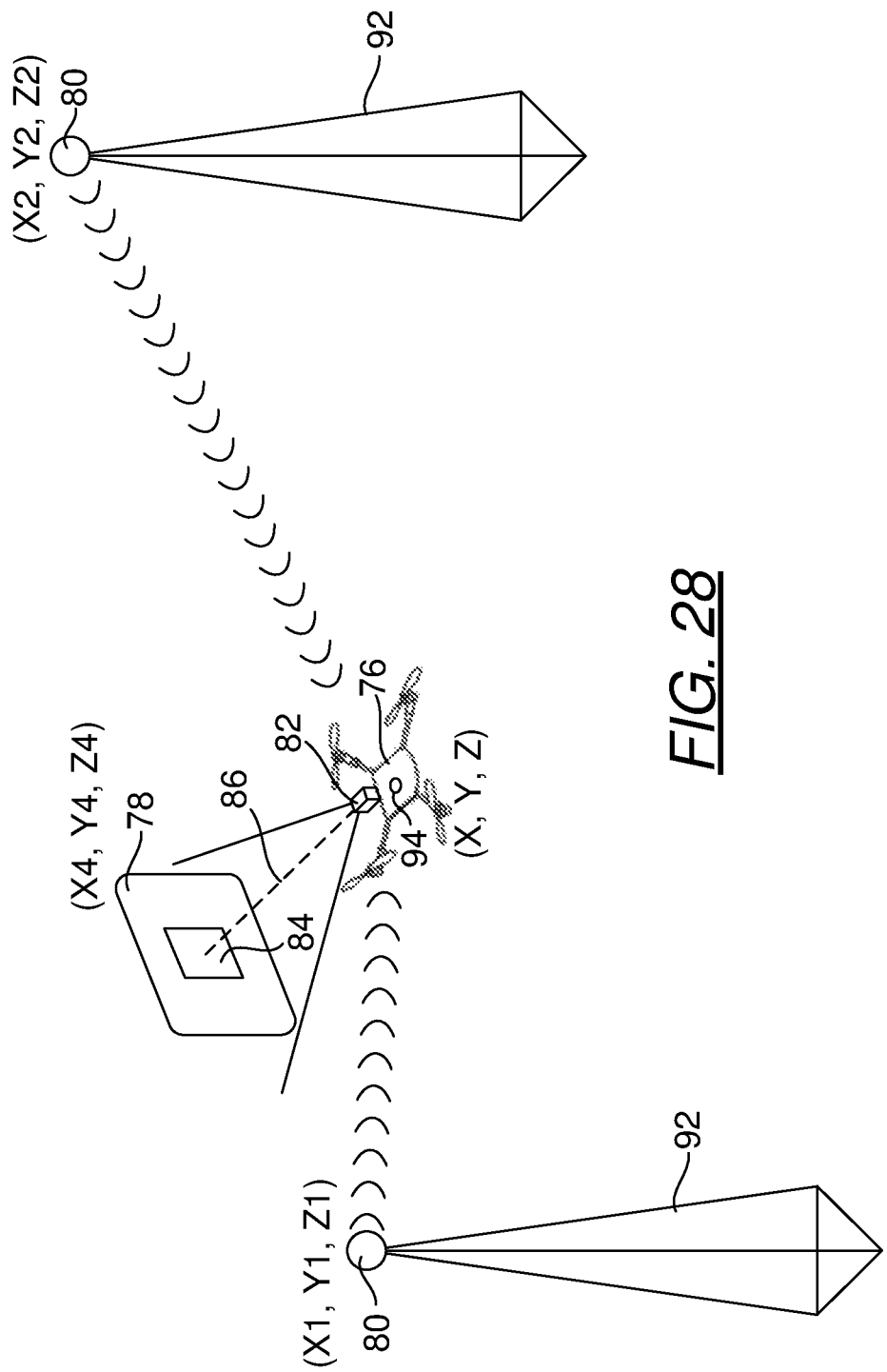
FIG. 28 is a diagram depicting a frequency calibration mechanism for identifying the signals a frequency receiver device is configured to receive in an environment containing two frequency originator devices.
Figure 29:
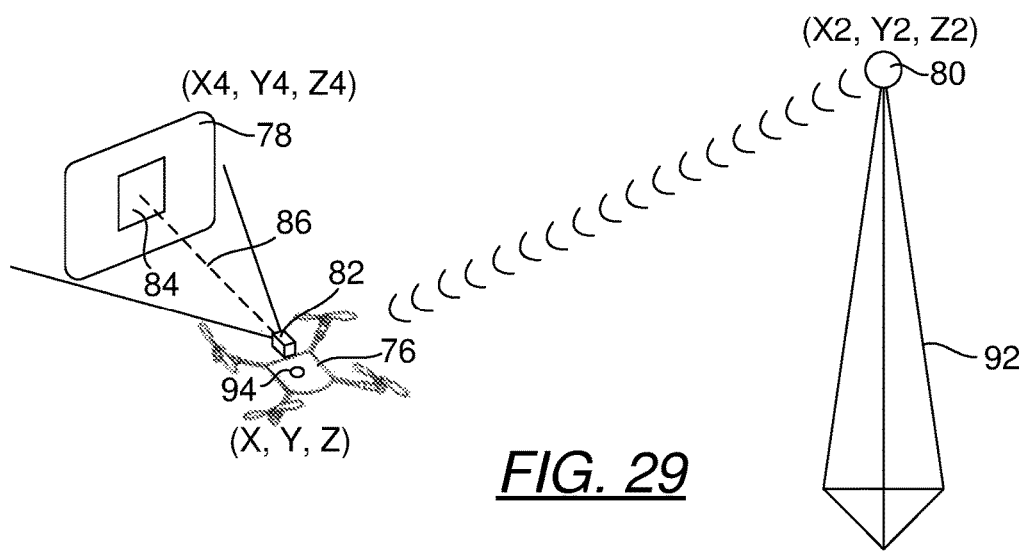
FIG. 29 is a diagram depicting a frequency calibration mechanism for updating the signals a frequency receiver device is configured to receive in an environment containing one frequency originator device.

FIG. 28 is a diagram depicting a frequency calibration mechanism for identifying the signals a frequency receiver device is configured to receive in an environment containing two frequency originator devices. FIG. 29 is a diagram depicting a frequency calibration mechanism for updating the signals a frequency receiver device is configured to receive in an environment containing one frequency originator device. Without an additional constraint, the absolute location of the frequency receiver device may not be determined when it is functionally coupled to less than three frequency originator devices. The application of additional requirements, such as the need for a vehicle hosting the frequency receiver device to be confined to a path, the use of a compass or magnetometer and/or the use of a homing routine may remove the need for three frequency originator devices.

Figure 30:
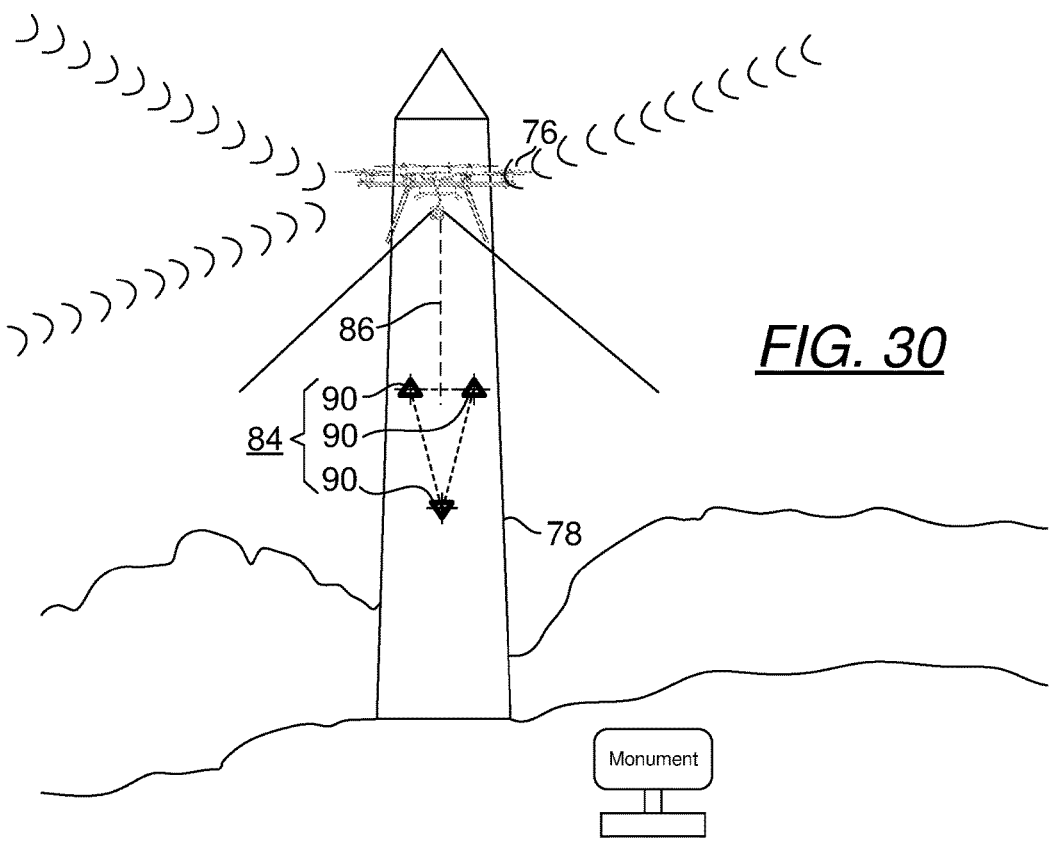
FIG. 30 is a diagram depicting one example of a visually unique object containing a visually unique pattern.

FIG. 30 is a diagram depicting one example of a visually unique object containing a visually unique pattern. In shall be noted that the use of a visually unique pattern 84 for calibration of a frequency receiver device is not limited to purpose-built towers and signs, etc. In this case, the visually unique object 78 is a monument containing a specific pattern, e.g., in this case, three triangular windows or markers 90 may be designated a visually unique pattern which can be readily visually detected such that pertinent information for the calibration of the frequency receiver device hosted on the vehicle 76 can be obtained.

Figure 31:
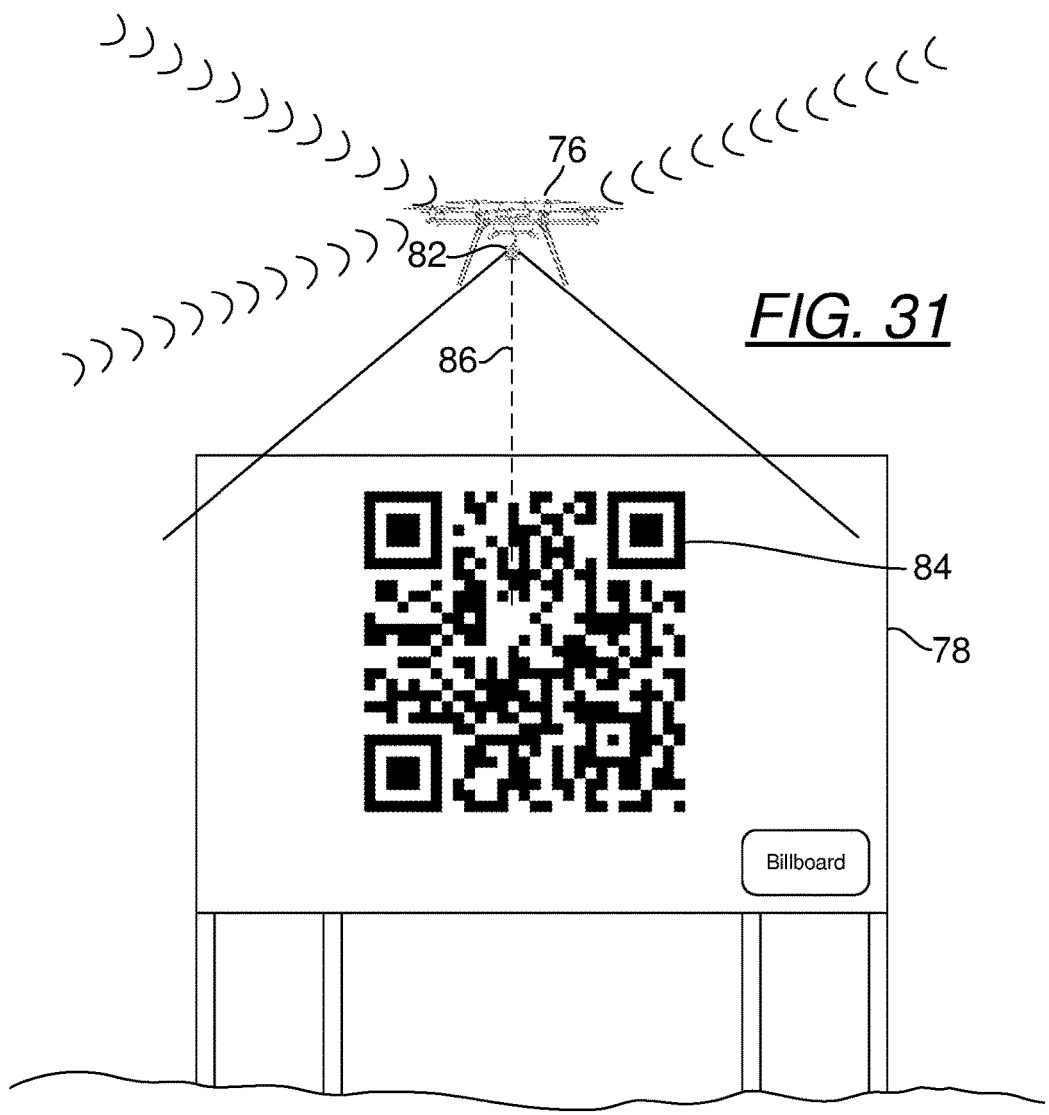
FIG. 31 is a diagram depicting another example of a visually unique object containing a visually unique pattern.

FIG. 31 is a diagram depicting another example of a visually unique object containing a visually unique pattern. In this example, the visually unique object 78 is a billboard containing a Quick Response (QR) code. The QR code can serve merely as a visually unique pattern or it can additionally indicate a Universal Resource Locator (URL) which provides a lookup table for pertinent information for the calibration of a frequency receiver device hosted on the vehicle 76.

Figure 32:
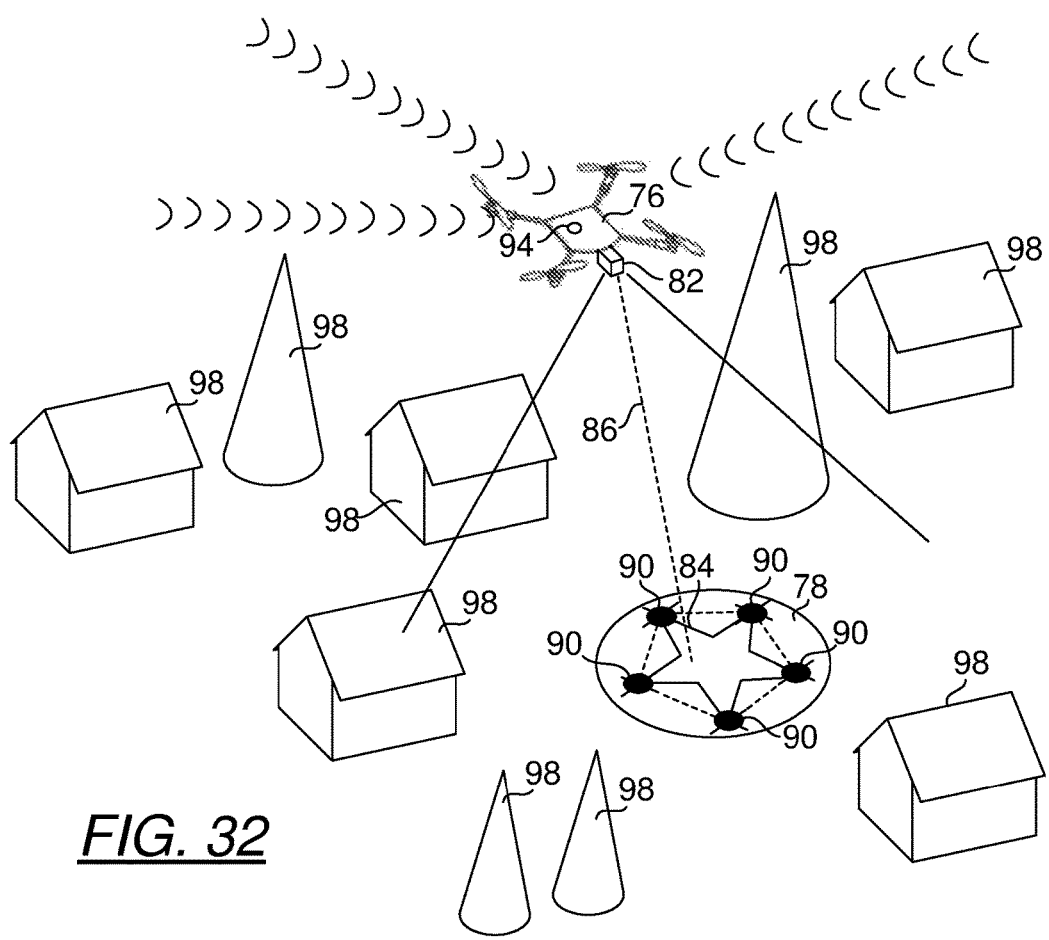
FIG. 32 is a diagram depicting yet another example of a visually unique object containing a visually unique pattern.
Figure 33:
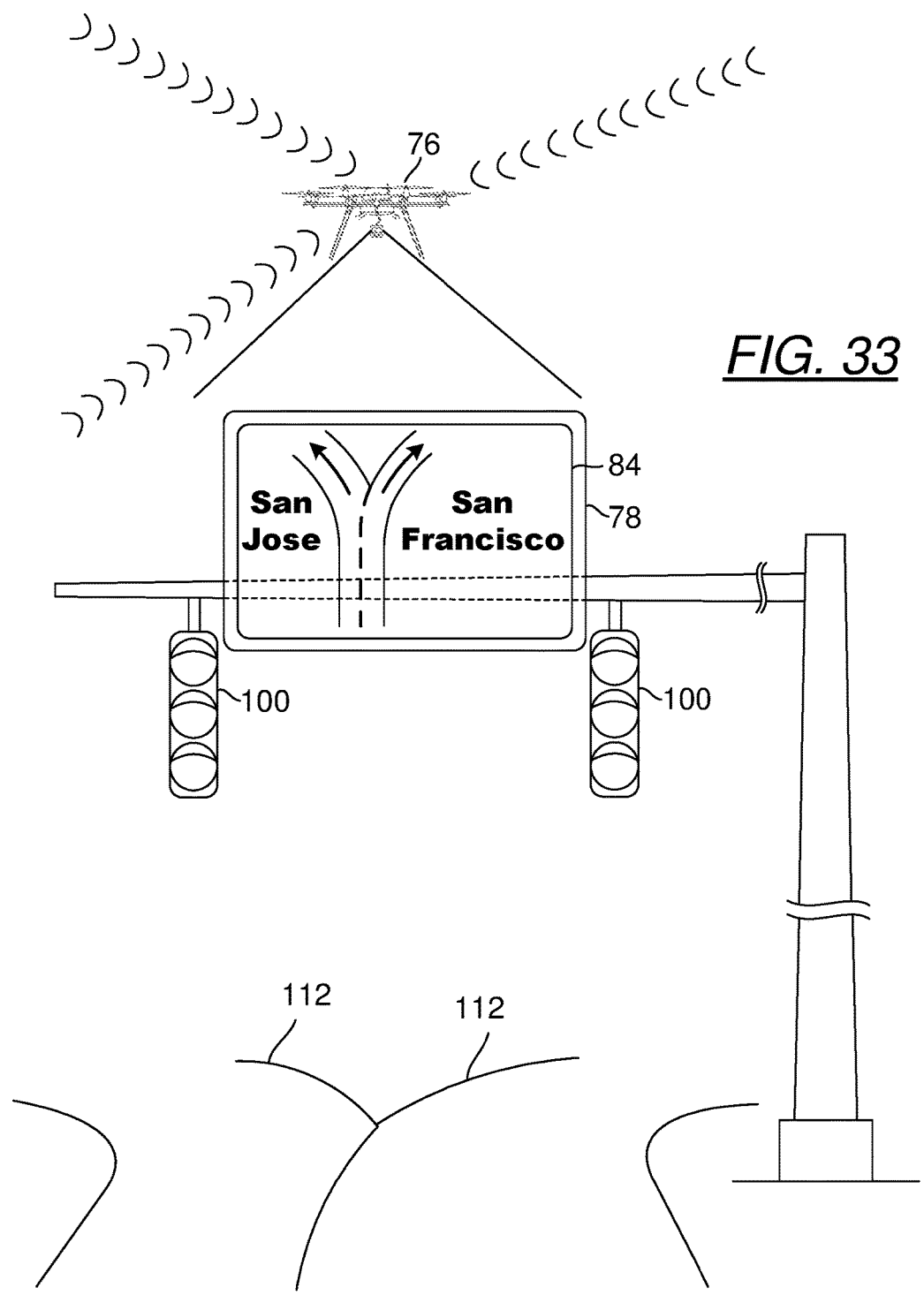
FIG. 33 is a diagram depicting yet another example of a visually unique object containing a visually unique pattern.

FIG. 32 is a diagram depicting yet another example of a visually unique object containing a visually unique pattern. In this example, the visually unique object 78 is a garden having a star-shaped centerpiece disposed among other objects, e.g., trees and buildings or houses 98. FIG. 33 is a diagram depicting yet another example of a visually unique object containing a visually unique pattern. In this case, the visually unique object 78 is a traffic sign. The visually unique pattern is a combination of words and a diagram depicting traffic directions. Additionally, traffic control devices, e.g., traffic lights 100, may also be used as supplements to aid in the detection of the traffic sign. This example further illustrates the use of normal existing roadways as paths for the aerial vehicles. The use of existing infrastructure for ground transportation including navigation and mapping capabilities, eliminates the need for dedicated aerial maps or paths. By using the same infrastructure for road or other ground vehicles, there are no potential privacy concerns that would need to be addressed as aerial vehicles are not configured to fly at a low altitude over populated areas, e.g., houses, buildings where access to ground transportation is unavailable. In this example, an analysis of an image obtained of the traffic control device depicted will result in the aerial vehicle confronted with two choices, i.e., taking a left turn to "San Jose" and taking a right turn to "San Francisco." Automatic feature (e.g., arrows, text) detections from images are used to resolve the instructions provided by the sign. The left sign which curves to the left is interpreted as an instruction for the traffic to take the left lane to proceed to "San Jose," which is the text that appears closest to this arrow. By the same token, the right sign which curves to the right is interpreted as an instruction for the traffic to take the right lane to proceed to "San Francisco," which is the text that appears closest to this arrow. Although it is inconsequential to select the exact lane over which the aerial vehicle hovers, the sign provides an instruction related to the direction which the aerial vehicle should be headed based on the destination or waypoint of the path. In one embodiment, without the benefit of a map of an area, based either on GPS or the present localization methods disclosed elsewhere herein, navigation can still occur based on guidance resulted from processing of images obtained of roadways 112 and road or other ground signs during travel of the aerial vehicle.

Figure 34:
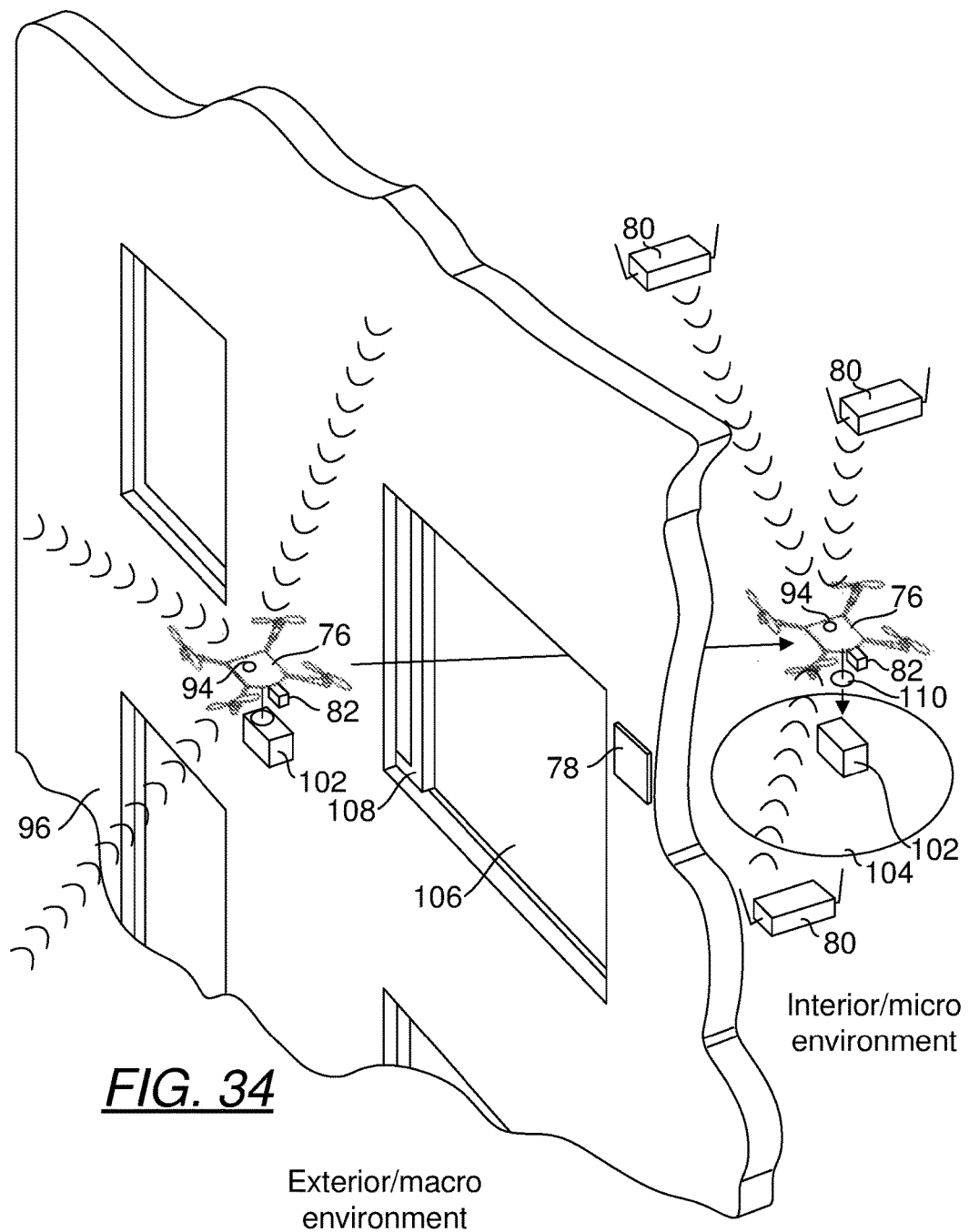
FIG. 34 is a diagram depicting one embodiment of a frequency calibration mechanism for identifying the signals a frequency receiver device is configured to receive in a first environment and the transition of the frequency receiver device from the first environment to a second environment as guided by the results of the frequency calibration mechanism.
Figure 35:
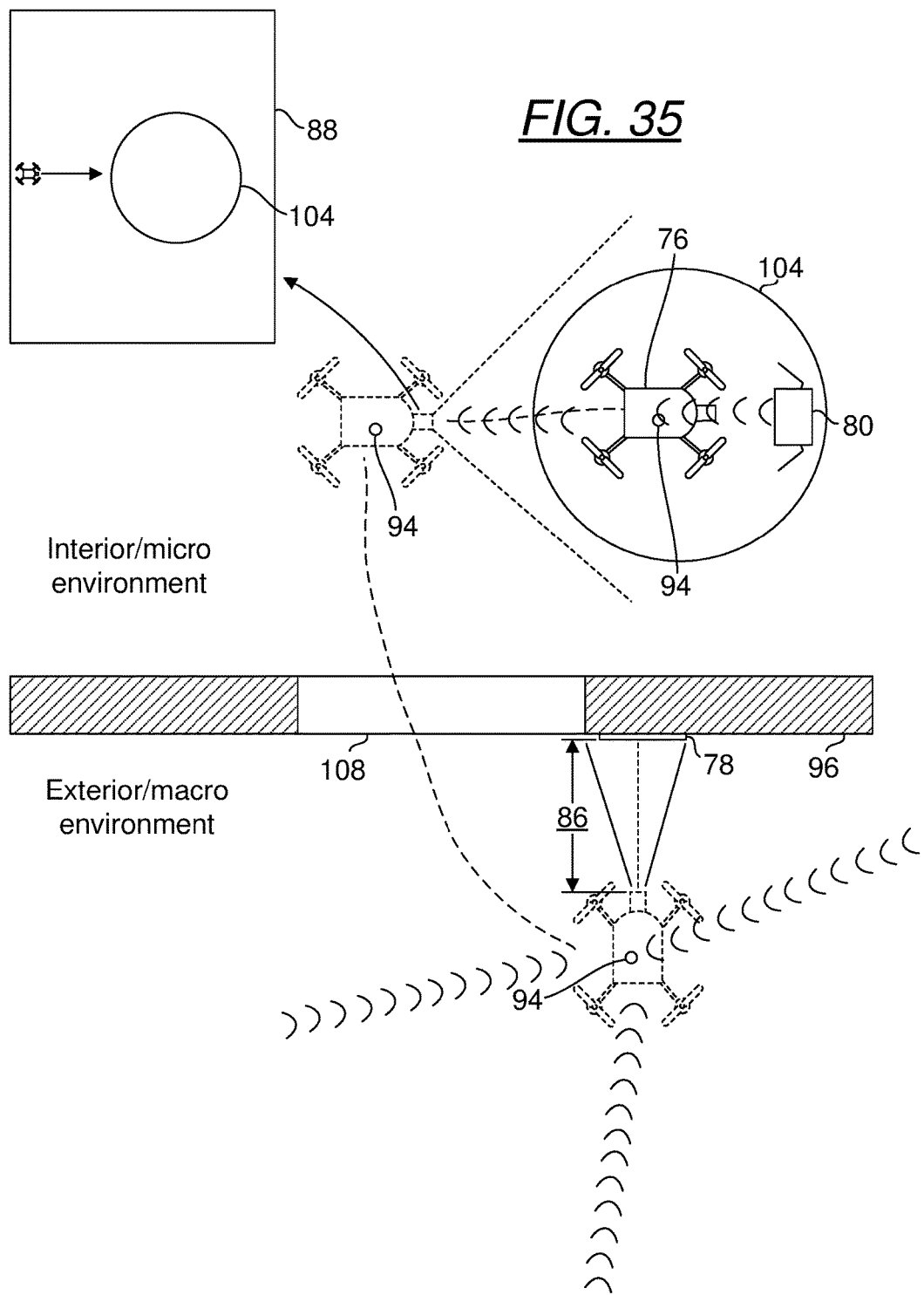
FIG. 35 is a diagram depicting another embodiment of a frequency calibration mechanism for identifying the signals a frequency receiver device is configured to receive in a first environment and the transition of the frequency receiver device from the first environment to a second environment as guided by the results of the frequency calibration mechanism.

In yet another embodiment, navigation is based on railways and signs associated with the railways. In yet another embodiment, navigation is based on geographical features, e.g., bodies of water (rivers, streams, etc.), mountains, hills and ridges, etc. In some aspects, navigation according to these latter modes is beneficial because railways are often continuous paths having man-made structures without a large number of signs, rendering image processing less computationally intensive and feature detection less error-prone. In one embodiment, with the benefit of a map of an area, based on GPS or the present localization methods disclosed elsewhere herein, existing and ubiquitous ground navigation systems can be adopted. For instance, an aerial vehicle will be guided using a two-dimensional navigation data for lateral position guidance. The aerial vehicle is flown at an elevation deemed suitable to clear existing obstacles, e.g., buildings, towers, traffic signs and control devices, etc., such that its altitude can be maintained without excessive altitude adjustments during its travel. In one embodiment, navigation is performed with the aid of a ground navigation map with GPS localization and/or the present localization method and feature detections as disclosed in FIG. 32. The latter is used for verifying that the aerial vehicle is travelling in the right path from time to time. For instance, if an aerial vehicle has travelled for an amount of time within which a sign should have been detected but has not been detected, the aerial vehicle should perform a routine to seek help or to attempt to locate itself. A ground navigation map includes, but not limited to, a map which includes instructions on how to arrive at a destination, typically via roadway, on foot or via any ground transportation pathways. Without the use of GPS for navigation, the onboard power of an aerial vehicle can be conserved, making the aerial vehicle capable of travelling greater distances without recharging. Further, the concept of navigation to the interior spaces of an address is disclosed. As a practical example, the delivery of an item to an apartment unit in a high rise can currently be made to the receiving point that is typically located at the road or ground level of the high rise. Provisions are typically required to be made for an occupant of the high rise for receiving a delivery, e.g., food or medicine, e.g., the recipient of item must collect the item at the point of delivery at the ground level. GPS-based navigation within a building can be challenging as GPS signals may not be available or they may be obscured. FIGS. 34 and 35 disclose examples where direct delivery of such an item can be accomplished.

FIG. 34 is a diagram depicting one embodiment of a frequency calibration mechanism for identifying the signals a frequency receiver device is configured to receive in a first environment and the transition of the frequency receiver device from the first environment to a second environment as guided by the results of the frequency calibration mechanism. It shall be noted in this example, there is a "hand-off" between the set of frequency originator devices located outside of the building 96 and the set located within the building 96. A vehicle 76 may be programmed to navigate to a particular address. Upon arriving at the address and detecting a relevant visually unique object 78, the pertinent information for calibration is then determined such that clock synchronization of the frequency receiver device 94 (disposed on the vehicle 76) with the set of frequency originator devices 80, e.g., Wi-Fi routers, at the interior space of the address, can occur. For a delivery to an interior space, a passageway 106 may be provided by leaving a window 108 to the interior space open. The vehicle may then be programmed to advance to a specified location to drop the delivery 102 at a delivery portal 104 upon activation of the delivery dispense control device 110. In one embodiment, a visually unique pattern is associated with one or more path instructions for the vehicle 76 when transitioning from a macro or exterior environment to a micro or interior environment. In this case, the instruction for the vehicle 76 is to look for an opened window. In one instance, the image acquisition device 82 is configured to recognize a window as a multi-corner shape as the window has four corners. A centerline path that is penetrating a plane bounded by the four corners can be calculated. In one embodiment, an additional obstacle detection device, e.g., a transceiver is useful for verifying that a planned path is free from obstacles. For instance, a weak signal is broadcast in the direction of a planned path. If a return signal is received as the transmitted weak signal is reflected by a nearby object, e.g., a window, an obstacle is determined to exist in the planned path. Otherwise, the vehicle may be programmed to proceed on the planned path. As shown in FIG. 34, the planned path is unobstructed and the vehicle 76 can thus proceed as planned.

FIG. 35 is a diagram depicting another embodiment of a frequency calibration mechanism for identifying the signals a frequency receiver device is configured to receive in a first environment and the transition of the frequency receiver device from the first environment to a second environment as guided by the results of the frequency calibration mechanism. Again, it shall be noted in this example that there is a "hand-off" between the set of frequency originator devices located outside of the building 96 and the set located within the building 96. In this example, however, two other means of navigation are possible. First, the vehicle's imaging system may be configured to detect a delivery portal 104 of a particular shape, e.g., in this case, circular, via images 88 obtained of the delivery portal and the vehicle is driven over the portal 104 before dropping the delivery atop the portal 104. Second, a single frequency originator device 80 may be used to guide the vehicle 76 where the vehicle is guided in the direction of diminishing distance between the frequency receiver device 94 and the frequency originator device 80.

Figure 36:
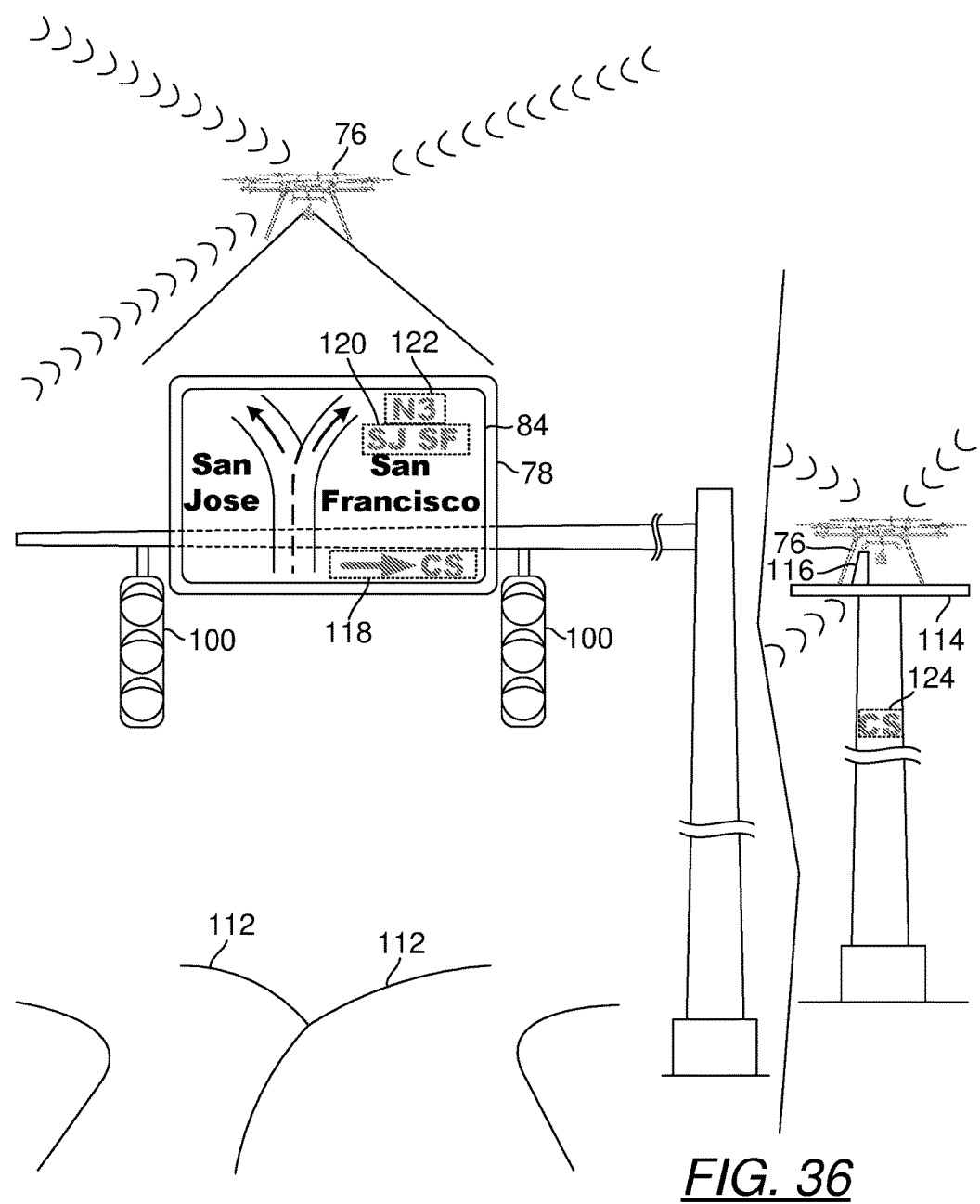
FIG. 36 is a diagram depicting a traffic sign and information disposed on the traffic sign for guiding an aerial vehicle in its ensuing journey or to receive power.
Figure 37:
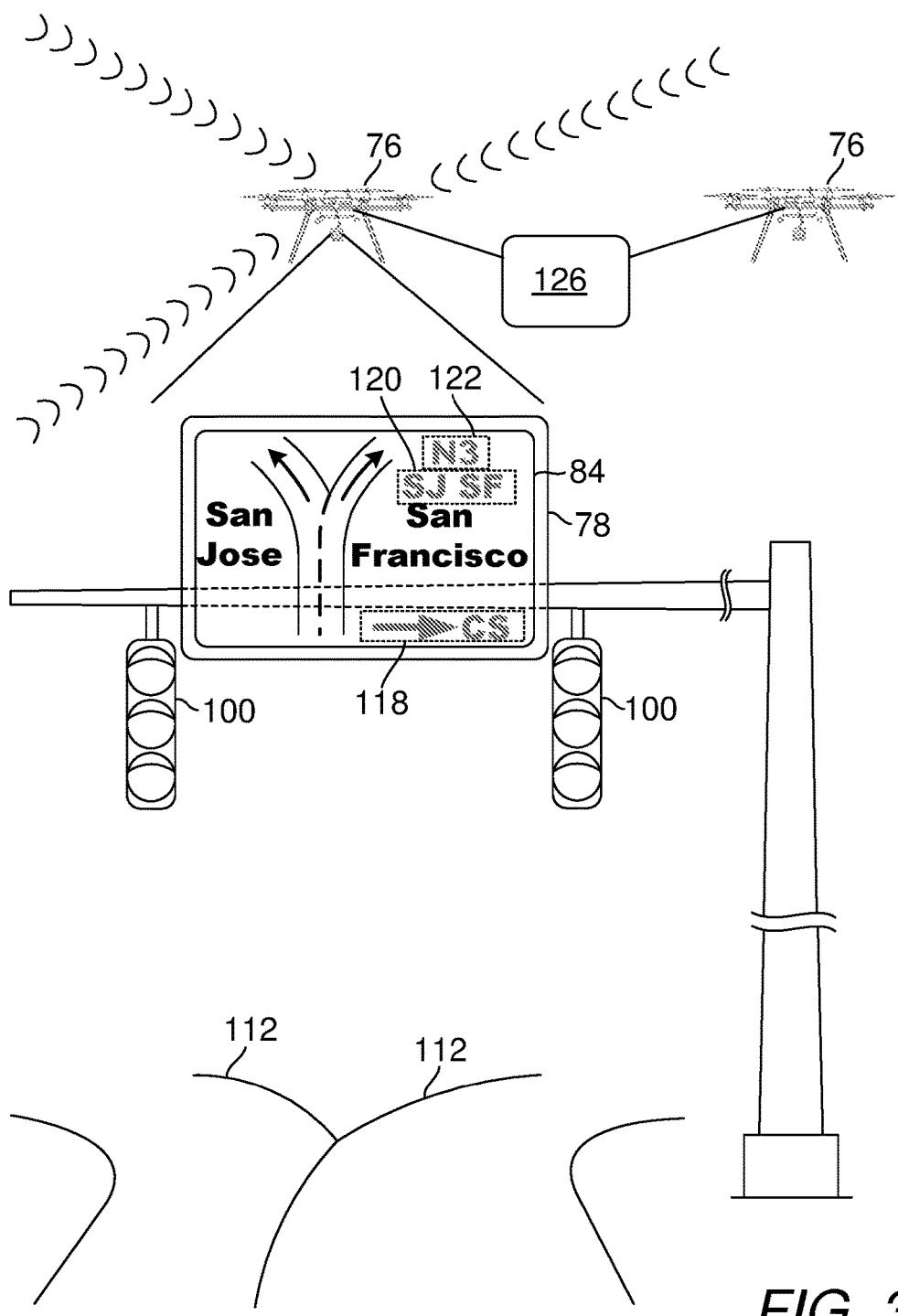
FIG. 37 is a diagram depicting a method by which multiple aerial vehicles cooperate to perform a task.

FIG. 36 is a diagram depicting a traffic sign and information disposed on the traffic sign for guiding an aerial vehicle in its ensuing journey or to receive power. In the embodiment shown, navigation is guided via markers or instructions invisible to the naked eye but visible to a specific imager coupled to an image processing system. In one embodiment, the markers are provided in invisible paint and the imager is an infrared imager. Such additional markers are invisible to drivers who share the roadways and therefore do not pose distraction risks to the drivers. However, such additional markers will enable the aerial vehicle equipped with an infrared imager to pick out its messages embedded in the traffic signs or other objects more readily, i.e., with or without little prior image acquisition training. In optical feature detection, in order to increase the likelihood that particular markers or features are picked out accurately from scenes or images, image processing devices are taught the association of specific features with specific shapes, sizes, fonts, colors, etc. In this example, the features to be detected will "stand out" as the imager picks out only features apparent in the infrared range. In this example, the first marker "N3" (designated as 122) may be used to indicate that the "next" traffic sign will be "3" miles from the current traffic sign. Therefore, although the aerial vehicle may continue to use its imager/s to navigate to the next traffic sign, it does not need to process the images for the specific markers/instructions for about the next three miles, further saving a number of activities which consume its on-board energy and shortening the duration to replenish on-board storage of energy or lengthening the distance that can be covered in a single replenishment of energy. Further, a marker, e.g., "SJ SF," may be used to indicate that in order to go to "San Jose," one must follow the "left" path as "SJ" is disposed to the left of "SF." By the same token, the path to "San Francisco" is the one on the right as "SF" is disposed to the right of "SJ." Further, a right-pointing arrow coupled with a label "CS" (designated as 118) may be used to indicate that a battery charging station 114 is located nearby and to the right of the marker. A marker "CS" (designated as 124) may be used to indicate that a structure is a charging station. In one example, a symbol is disposed atop the charging station to indicate that the structure is a platform upon which an electrically-powered aerial vehicle to be parked to be interfaced with a charger 116. In one embodiment, a charging station is equipped with a battery exchanging device configured to remove the battery pack of a parked aerial vehicle and insert a fully-charged battery in the parked aerial vehicle, alleviating the need for the aerial vehicle to be parked for an extended duration to be charged. In one embodiment, the navigation methods disclosed elsewhere herein that involve traffic signs are applicable to delivery of goods from a first traffic sign to a second traffic sign. In circumstances where no specific data is available for more precise delivery of goods, e.g., directly to specific locations, e.g., apartments, other types of single-level or multi-level dwellings and businesses, navigation for the purpose of delivery of goods to a traffic sign is a viable solution. In circumstances where the delivery of goods is made to a public location, the authentication of receipt of deliveries becomes critical. In other words, the delivery of goods should be made to their rightful recipients. In one embodiment, a short range wireless communication tool configured for a protocol, e.g., Bluetooth®, is used to authenticate that the recipient is nearby. The aerial vehicle may be equipped with a transceiver of short range wireless communication. A recipient may communicate his or her presence using a mobile device having a matching transceiver. The aerial vehicle is guided towards the source of a short range wireless communication signal by following a direction in which the signal strengthens (as the gap between the aerial vehicle and the mobile device diminishes). Further, in one embodiment, aerial vehicle-to-aerial vehicle communication is made available such that multiple aerial vehicles may cooperate to make a concerted delivery and make travel of the aerial vehicles more secure, etc. In one instance, if two aerial vehicles are headed to the same location, a head aerial vehicle may be used to "lead" the second aerial vehicle. If the second aerial vehicle is allowed to be led by the first aerial vehicle, it will simply "follow" the first vehicle which again, does not require the use of GPS and other navigation means, further conserving energy stored on the second aerial vehicle. Further, there may be goods which exceed the payload of a single aerial vehicle. FIG. 37 is a diagram depicting a method by which multiple aerial vehicles cooperate to perform a task. In this case, the payload is collectively met by more than one aerial vehicle. Again, a first aerial vehicle acts as a lead vehicle while sharing a load 126 with a second aerial vehicle which simply follows the first aerial vehicle while sharing the burden of the load with the first aerial vehicle.

In one embodiment, markers may be disposed on surfaces of roadways or paths to aid the navigation of aerial vehicles. Markers may be disposed at fixed or varying intervals to indicate the directions to cities, road names, the rules for unmanned aerial vehicles, etc. Aerial vehicles equipped with image processing systems are configured to point their imagers downwardly to obtain images of the markers such that further instructions can be determined for the navigation of the aerial vehicles.

While the methods, systems and devices have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications are referenced. The disclosures of these publications in their entireties are hereby incorporated by reference into this application in order to more fully describe the state of the art to which the methods and systems pertain.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following inventive concepts.

What is claimed herein is:

1. A method for navigating an aerial vehicle having an image processing system and a frequency receiver device from a first location to a second location, wherein the aerial vehicle having a localization system, said method comprising guiding the aerial vehicle according to a ground navigation map from the first location to the second location; and further comprising:
   (a) visually detecting a feature indicating an opening upon arriving at an intermediate location between the first location and the second location;
   (b) visually guiding the aerial vehicle through said opening from said intermediate location;
   (c) upon passing said opening, functionally engaging the frequency receiver device of the aerial vehicle with at least three frequency originator devices of known location to yield a relative location of the aerial vehicle with respect to said at least three frequency originator devices; and (d) guiding the aerial vehicle from said intermediate location to the second location based on closing a gap between said relative location of the aerial vehicle with respect to said at least three frequency originator devices and the second location.

2. The method of claim 1, further comprising guiding the aerial vehicle according to markers disposed on traffic signs and ground transportation pathways.

3. The method of claim 2, wherein said traffic signs comprises a marker selected from group consisting of a material visible to the naked eye and a material invisible to the naked eye.

4. The method of claim 1, wherein the aerial vehicle further having a short range wireless communication tool, said method further comprises guiding said aerial vehicle towards the source of a short range wireless communication signal at the second location.

5. The method of claim 1, further comprising guiding the aerial vehicle to a location between the first location and the second location for power replenishment such that the aerial vehicle completes its journey from the first location to the second location.

6. A method for navigating an aerial vehicle having an image processing system from a first location to a second location, wherein the aerial vehicle having a localization system, said method comprising guiding the aerial vehicle according to a ground navigation map from the first location to the second location; and further comprising:
   (a) visually detecting a feature indicating an opening upon arriving at an intermediate location between the first location and the second location;
   (b) visually guiding the aerial vehicle through said opening from said intermediate location; and
   (c) upon passing said opening, detecting an image of a pattern and upon detecting said pattern, guiding the aerial vehicle to close a gap between the aerial vehicle and the pattern.

7. A method for navigating an aerial vehicle from a first location to a second location, wherein the aerial vehicle having an image processing system and a frequency receiver device, said method comprising guiding the aerial vehicle according to markers disposed on traffic signs and ground transportation pathways from the first location to the second location by utilizing the image processing system; and further comprising:
   (a) visually detecting a feature indicating an opening upon arriving at an intermediate location between the first location and the second location;
   (b) visually guiding the aerial vehicle through said opening from said intermediate location;
   (c) upon passing said opening, functionally engaging the frequency receiver device of the aerial vehicle with at least three frequency originator devices of known location to yield a relative location of the aerial vehicle with respect to said at least three frequency originator devices; and
   (d) guiding the aerial vehicle from said intermediate location to the second location based on closing a gap between said relative location of the aerial vehicle with respect to said at least three frequency originator devices and the second location.

8. The method of claim 7, wherein the aerial vehicle further having a localization system, said method further comprises guiding the aerial vehicle according to a ground navigation map from the first location to the second location.

9. The method of claim 7, further comprising guiding the aerial vehicle to a location between the first location and the second location for power replenishment such that the aerial vehicle completes its journey from the first location to the second location.

10. The method of claim 7, wherein said markers are selected from the group consisting of a material visible to the naked eye and a material invisible to the naked eye.

11. The method of claim 7, wherein the aerial vehicle further having a short range wireless communication tool, said method further comprises guiding said aerial vehicle towards the source of a short range wireless communication signal at the second location.

12. A method for navigating an aerial vehicle from a first location to a second location, wherein the aerial vehicle having an image processing system, said method comprising guiding the aerial vehicle according to markers disposed on traffic signs and ground transportation pathways from the first location to the second location by utilizing the image processing system; and further comprising:
   (a) visually detecting a feature indicating an opening upon arriving at an intermediate location between the first location and the second location;
   (b) visually guiding the aerial vehicle through said opening from said intermediate location; and
   (c) upon passing said opening, detecting an image of a pattern and upon detecting said pattern, guiding the aerial vehicle to close a gap between the aerial vehicle and the pattern.

13. A method for navigating an aerial vehicle from a first location to a second location, wherein the aerial vehicle having an image processing system and a frequency receiver device, said method comprising guiding the aerial vehicle according to invisible markers disposed on traffic signs and ground transportation pathways from the first location to the second location by utilizing the image processing system; and further comprising:
   (a) visually detecting a feature indicating an opening upon arriving at an intermediate location between the first location and the second location;
   (b) visually guiding the aerial vehicle through said opening from said intermediate location;
   (c) upon passing said opening, functionally engaging a frequency receiver device of the aerial vehicle with at least three frequency originator devices of known location to yield a relative location of the aerial vehicle with respect to said at least three frequency originator devices; and
   (d) guiding the aerial vehicle from said intermediate location to the second location based on closing a gap between said relative location of the aerial vehicle with respect to said at least three frequency originator devices and the second location.

14. The method of claim 13, wherein the aerial vehicle further having a localization system, said method further comprises guiding the aerial vehicle according to a ground navigation map from the first location to the second location.

15. The method of claim 13, further comprising guiding the aerial vehicle to a location between the first location and the second location for power replenishment such that the aerial vehicle completes its journey from the first location to the second location.

16. The method of claim 13, wherein the aerial vehicle further having a short range wireless communication tool, said method further comprises guiding said aerial vehicle towards the source of a short range wireless communication signal at the second location.

17. A method for navigating an aerial vehicle from a first location to a second location, wherein the aerial vehicle having an image processing system, said method comprising guiding the aerial vehicle according to invisible markers disposed on traffic signs and ground transportation pathways from the first location to the second location by utilizing the image processing system; and further comprising:
- (a) visually detecting a feature indicating an opening upon arriving at an intermediate location between the first location and the second location;
- (b) visually guiding the aerial vehicle through said opening from said intermediate location; and
- (c) upon passing said opening, detecting an image of a pattern and upon detecting said pattern, guiding the aerial vehicle to close a gap between the aerial vehicle and the pattern.

* * * * *